United States Patent [19]

Harrison

[11] Patent Number: 5,112,507
[45] Date of Patent: May 12, 1992

[54] POLYMERIC DISPERSANTS HAVING ALTERNATING POLYALKYLENE AND SUCCINIC GROUPS

[75] Inventor: James J. Harrison, Novato, Calif.

[73] Assignee: Chevron Research and Technology Company, San Francisco, Calif.

[21] Appl. No.: 414,993

[22] Filed: Sep. 29, 1989

Related U.S. Application Data

[63] Continuation-in-part of Ser. No. 251,613, Sep. 29, 1988, abandoned.

[51] Int. Cl.$^5$ .................... C10M 149/10; C10L 1/22
[52] U.S. Cl. ................ 252/51.5 A; 252/56 D; 44/351; 44/346; 44/389; 44/393; 526/262; 548/546; 548/547; 549/233; 549/252; 560/190; 560/204; 562/590; 562/596
[58] Field of Search ........... 562/590, 596; 560/190, 560/204; 549/233, 252; 548/546, 547; 252/56 D, 51.5 A; 44/62, 63; 526/262

[56] References Cited

U.S. PATENT DOCUMENTS

| | | | |
|---|---|---|---|
| 2,977,334 | 3/1961 | Zopf, Jr. et al. | 252/56 D |
| 3,455,827 | 7/1969 | Mehmedbasich et al. | 548/546 |
| 3,677,725 | 7/1972 | Andress | 44/63 |
| 3,720,733 | 3/1973 | Rinkler et al. | 526/262 |
| 4,055,581 | 10/1977 | Hopkins et al. | 562/590 |
| 4,359,325 | 11/1982 | Dawans et al. | 252/56 D |
| 4,416,668 | 11/1983 | Thompson | 44/63 |
| 4,526,950 | 7/1985 | Grava | 562/590 |
| 4,548,725 | 10/1985 | Bridger | 252/56 D |
| 4,612,132 | 9/1986 | Wollenberg et al. | 548/547 |

FOREIGN PATENT DOCUMENTS

| | | | |
|---|---|---|---|
| 270671 | 11/1988 | Japan | 549/252 |
| 900599 | 1/1985 | U.S.S.R. | 549/252 |

Primary Examiner—Prince Willis, Jr.
Assistant Examiner—Ellen McAvoy
Attorney, Agent, or Firm—C. J. Caroli; R. C. Gaffney

[57] ABSTRACT

Novel copolymers of unsaturated acidic reactants and high molecular weight olefins wherein at least 20 percent of the total high molecular weight olefin comprises the alkylvinylidene isomer are useful as dispersants in lubricating oils and fuels and also may be used to prepare polysuccinimides and other post-treated additives useful in lubricating oils and fuels.

68 Claims, 1 Drawing Sheet

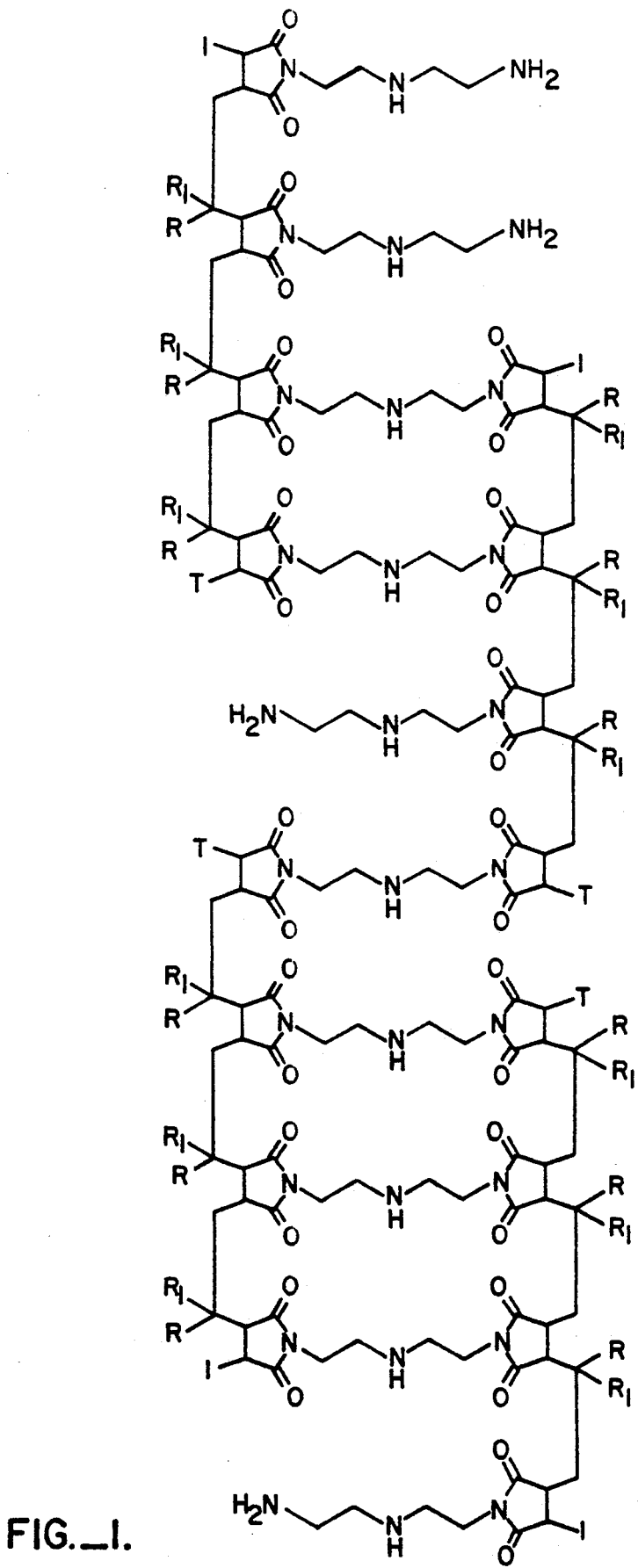
FIG.\_1.

POLYMERIC DISPERSANTS HAVING ALTERNATING POLYALKYLENE AND SUCCINIC GROUPS

CROSS-REFERENCE TO RELATED APPLICATIONS

This application is a continuation-in-part of U.S. application Ser. No. 251,613, filed Sept. 29, 1988, now abandoned.

BACKGROUND OF THE INVENTION

The present invention relates to compositions which are useful as intermediates for dispersants used in lubricating oil compositions or as dispersants themselves. In addition, some of these compositions are useful in the preparation of novel high molecular weight dispersants which have superior dispersant properties for dispersing sludge and varnish and superior Viton Seal compatibility.

The high molecular weight dispersants of the present invention also advantageously impart fluidity modifying properties to lubricating oil compositions which are sufficient to allow elimination of some proportion of viscosity index improver from multigrade lubricating oil compositions which contain these dispersants.

Alkenyl-substituted succinic anhydrides have been used as dispersants. Such alkenyl-substituted succinic anhydrides have been prepared by two different processes, a thermal process (see, e.g., U.S. Pat. No. 3,361,673) and a chlorination process (see, e.g., U.S. Pat. No. 3,172,892). The polyisobutenyl succinic anhydride ("PIBSA") produced by the thermal process has been characterized as a monomer containing a double bond in the product. Although the exact structure of chlorination PIBSA has not been definitively determined, the chlorination process PIBAs have been characterized as monomers containing either a double bond, a ring, other than a succinic anhydride ring and/or chlorine in the product. [See J. Weill and B. Sillion, "Reaction of Chlorinated Polyisobutene with Maleic Anhydride:Mechanism Catalysis by Dichloromaleic Anhydride", Revue de l'Institut Francais du Petrole, Vol. 40, No. 1, pp. 77-89 (January-February, 1985).] Such compositions include one-to-one monomeric adducts (see, e.g., U.S. Pat. Nos. 3,219,666; 3,381,022) as well as adducts having polyalkenyl-derived substituents adducted with at least 1.3 succinic groups per polyalkenyl-derived substituent (see, e.g., U.S. Pat. No. 4,234,435).

In addition, copolymers of maleic anhydrides and some aliphatic alpha-olefins have been prepared. The polymers so produced were useful for a variety of purposes including dispersants for pigments and intermediates in the preparation of polyesters by their reaction with polyols or polyepoxides. However, olefins having more than about 30 carbon atoms were found to be relatively unreactive. (See, e.g., U.S. Pat. Nos. 3,461,108; 3,560,455; 3,560,456; 3,560,457; 3,580,893; 3,706,704; 3,729,450; and 3,729,451).

SUMMARY OF THE INVENTION

The present invention is directed to novel compositions useful as additives which comprise copolymers of an unsaturated acidic reactant and high molecular weight olefin wherein at least about 20 percent of the total high molecular weight olefin comprises the alkylvinylidene isomer, said copolymers having alternating succinic and polyalkyl groups. The high molecular weight olefin has a sufficient number of carbon atoms such that the resulting copolymer is soluble in lubricating oil. Suitable olefins include those having about 32 carbon atoms or more (preferably having about 52 carbon atoms or more). Those preferred high molecular weight olefins include polyisobutenes. Especially preferred are polyisobutenes having average molecular weights of from about 500 to about 5000 and in which the alkylvinylidene isomer comprises at least 50 percent of the total olefin.

These copolymers are useful as dispersants themselves and also as intermediates in the preparation of other dispersant additives having improved dispersancy and/or detergency properties when employed in a lubricating oil.

These copolymers are also advantageous because they do not contain double bonds, rings, other than succinic anhydride rings, or chlorine (in contrast to thermal and chlorination PIBSAs) and as such have improved stability, as well as improved environmental properties due to the absence of chlorine.

The present invention is also directed to polysuccinimides which are prepared by reacting a copolymer of the present invention with a polyamine to give a polysuccinimide. The present invention is directed to mono-polysuccinimides (where a polyamine component reacts with one succinic group); bis-polysuccinimides (where a polyamine component reacts with a succinic group from each of two copolymer molecules, thus effectively cross-linking the copolymer molecules); and higher polysuccinimides (where a polyamine component reacts with a succinic group from each of greater than 2 copolymer molecules). These polysuccinimides are useful as dispersants and/or detergents in fuels and oils. In addition, these polysuccinimides have advantageous viscosity modifying properties, and may provide a viscosity index credit ("V.I. Credit") when used in lubricating oils, which may permit elimination of some portion of viscosity index improver ("V.I. Improver") from multigrade lubricating oils containing the same.

In addition, the polysuccinimides of the present invention can form a ladder polymeric structure or a cross-linked polymeric structure. These structures are advantageous because it is believed such structures are more stable and resistant to hydrolytic degradation and also to degradation by shear stress.

In addition, the present invention is directed to modified polysuccinimides wherein one or more of the nitrogens of the polyamine component is substituted with a hydrocarbyl oxycarbonyl, a hydroxyhydrocarbyl oxycarbonyl or a hydroxy poly(oxyalkylene)-oxycarbonyl. These modified polysuccinimides are improved dispersants and/or detergents for use in fuels or oils.

Accordingly, the present invention also relates to a lubricating oil composition comprising a major amount of an oil of lubricating viscosity and an amount of a copolymer, polysuccinimide or modified succinimide additive of the present invention sufficient to provide dispersancy and/or detergency. The additives of the present invention may also be formulated in lubricating oil concentrates which comprise from about 90 to about 50 weight percent of an oil of lubricating viscosity and from about 10 to about 50 weight percent of an additive of the present invention.

Another composition aspect of the present invention is a fuel composition comprising a major portion of a fuel boiling in a gasoline or diesel range and an amount of copolymer, polysuccinimide or modified succinimide additives sufficient to provide dispersancy and/or detergency. The present invention is also directed to fuel concentrates comprising an inert stable oleophilic organic solvent boiling in the range of about 150° F. to about 400° F. and from about 5 to about 50 weight percent of an additive of the present invention.

Definitions

As used herein, the following terms have the following meanings unless expressly stated to the contrary.

The term "unsaturated acidic reactants" refers to maleic or fumaric reactants of the general formula:

(II)

wherein X and X' are the same or different, provided that at least one of X and X' is a group that is capable of reacting to esterify alcohols, form amides or amine salts with ammonia or amines, form metal salts with reactive metals or basically reacting metal compounds and otherwise function as acylating agents. Typically, X and/or X, is —OH, —O—hydrocarbyl, —OM+ where M+ represents one equivalent of a metal, ammonium or amine cation, —NH$_2$, —Cl, —Br. and taken together X and X' can be —O— so as to form an anhydride. Preferably X and X' are such that both carboxylic functions can enter into acylation reactions. Maleic anhydride is a preferred unsaturated acidic reactant. Other suitable unsaturated acidic reactants include electron-deficient olefins such as monophenyl maleic anhydride; monomethyl, dimethyl, monochloro, monobromo, monofluoro, dichloro and difluoro maleic anhydride; N-phenyl maleimide and other substituted maleimides; isomaleimides; fumaric acid, maleic acid, alkyl hydrogen maleates and fumarates, dialkyl fumarates and maleates, fumaronilic acids and maleanic acids; and maleonitrile, and fumaronitrile.

The term "alkylvinylidene" or "alkylvinylidene isomer" refers to high molecular weight olefins and polyalkylene components having the following vinylidene structure

(III)

wherein R is alkyl or substituted alkyl of sufficient chain length to give the resulting molecule solubility in lubricating oils and fuels, thus R generally has at least about 30 carbon atoms, preferably at least about 50 carbon atoms and $R_v$ is lower alkyl of about 1 to about 6 carbon atoms.

The term "soluble in lubricating oil" refers to the ability of a material to dissolve in aliphatic and aromatic hydrocarbons such as lubricating oils or fuels in essentially all proportions.

The term "high molecular weight olefins" refers to olefins (including polymerized olefins having a residual unsaturation) of sufficient molecular weight and chain length to lend solubility in lubricating oil to their reaction products. Typically olefins having about 32 carbons or greater (preferably olefins having about 52 carbons or more) suffice.

The term "high molecular weight polyalkyl" refers to polyalkyl groups of sufficient molecular weight and hydrocarbyl chain length that the products prepared having such groups are soluble in lubricating oil. Typically these high molecular weight polyalkyl groups have at least about 30 carbon atoms, preferably at least about 50 carbon atoms. These high molecular weight polyalkyl groups may be derived from high molecular weight olefins.

The term "PIBSA" is an abbreviation for polyisobutenyl succinic anhydride.

The term "polyPIBSA" refers to a class of copolymers within the scope of the present invention which are copolymers of polyisobutene and an unsaturated acidic reactant which have alternating succinic groups and polyisobutyl groups. PolyPIBSA has the general formula

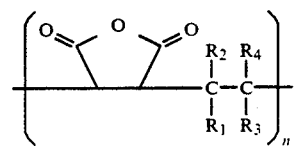

wherein n is one or greater; $R_1$, $R_2$, $R_3$ and $R_4$ are selected from hydrogen, methyl and polyisobutyl having at least about 30 carbon atoms (preferably at least about 50 carbon atoms) wherein either $R_1$ and $R_2$ are hydrogen and one of $R_3$ and $R_4$ is methyl and the other is polyisobutyl, or $R_3$ and $R_4$ are hydrogen and one of $R_1$ and $R_2$ is methyl and the other is polyisobutyl.

The term "PIBSA number" refers to the anhydride (succinic group) content of polyPIBSA on a 100% actives basis. The PIBSA number is calculated by dividing the saponification number by the percent polyPIBSA in the product. The units are mg KOH per gram sample.

The term "succinic group" refers to a group having the formula

wherein W and Z are independently selected from the group consisting of —OH, —Cl, —O— lower alkyl or taken together are —O— to form a succinic anhydride group.

The term "degree of polymerization" expresses the length of a linear polymer and refers to the number of repeating (monomeric) units in the chain. The average molecular weight of a polymer is the product of the degree of polymerization and the average molecular weight of the repeating unit (monomer). Accordingly, the average degree of polymerization is calculated by dividing the average molecular weight of the polymer by the average molecular weight of the repeating unit.

The term "polysuccinimide" refers to the reaction product of a copolymer of the present invention with polyamine.

BRIEF DESCRIPTION OF THE DRAWING

FIG. 1 depicts one embodiment of a polysuccinimide of the present invention, wherein R is polyisobutyl, $R_1$ is lower alkyl, I is an initiator group and T is a terminator group.

DETAILED DESCRIPTION OF THE INVENTION

A. COPOLYMER

The copolymers of the present invention are prepared by reacting a high molecular weight olefin wherein at least about 20% of the total olefin composition comprises the alkylvinylidene isomer and an unsaturated acidic reactant in the presence of a free radical initiator. Suitable high molecular weight olefins have a sufficient number of carbon atoms so that the resulting copolymer is soluble in lubricating oil and thus have on the order of about 32 carbon atoms or more. Preferred high molecular weight of olefins are polyisobutenes and polypropylenes. Especially preferred are polyisobutenes, particularly preferred are those having a molecular weight of about 500 to about 5000, more preferably about 900 to about 2500. Preferred unsaturated acidic reactants include maleic anhydride.

Since the high molecular weight olefins used to prepare the copolymers of the present invention are generally mixtures of individual molecules of different molecular weights, individual copolymer molecules resulting will generally contain a mixture of high molecular weight polyalkyl groups of varying molecular weight. Also, mixtures of copolymer molecules having different degrees of polymerization will be produced.

The copolymers of the present invention have an average degree of polymerization of 1 or greater, preferably from about 1.1 to about 20, and more preferably from about 1.5 to about 10.

Among other factors, the present invention is based on my surprising finding that the reaction of these high molecular weight olefins wherein at least about 20% of the total composition comprises the methylvinylidene isomer with an unsaturated acidic reactant in the presence of a free radical initiator results in a copolymer having alternating polyalkylene and succinic groups. This is surprising in view of the teachings that reaction of polyalkenes, such as polyisobutenes, with unsaturated acidic reactants such as maleic anhydride, in the presence of a free radical initiator, resulted in a product similar to that produced by the thermal process for PIBSA which is a monomeric one-to-one adduct (see, e.g., U.S. Pat. No. 3,367,864). It was taught that high molecular weight olefins were relative unreactive under those conditions which was confirmed by my findings that reaction of polyisobutene prepared using AlCl₃ catalysis [in which the alkylvinylidene isomer comprised a very small proportion (less than about 10%) of the total composition] with maleic anhydride in the presence of a free radical initiator resulted in low yield of product. In addition, the product obtained was similar to thermal PIBSA in molecular weight.

Thus, the copolymers of the present invention are prepared by reacting a "reactive" high molecular weight olefin in which a high proportion of unsaturation, at least about 20% is in the alkylvinylidene configuration, e.g.

wherein R and R$_v$ are as previously defined in conjunction with Formula III, with an unsaturated acidic reactant in the presence of a free radical initiator. The product copolymer has alternating polyalkylene and succinic groups and has an average degree of polymerization of 1 or greater.

The copolymers of the present invention have the general formula:

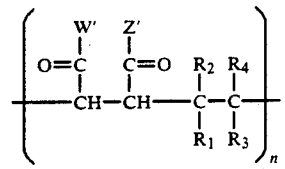

wherein W' and Z' are independently selected from the group consisting of —OH, —O— lower alkyl or taken together are —O— to form a succinic anhydride group, n is one or greater; and R$_1$, R$_2$, R$_3$ and R$_4$ are selected from hydrogen, lower alkyl of 1 to 6 carbon atoms, and high molecular weight polyalkyl wherein either R$_1$ and R$_2$ are hydrogen and one of R$_3$ and R$_4$ is lower alkyl and the other is high molecular weight polyalkyl, or R$_3$ and R$_4$ are hydrogen and one of R$_1$ and R$_2$ is lower alkyl and the other is high molecular weight polyalkyl.

In a preferred embodiment, when maleic anhydride is used as the unsaturated acidic reactant, the reaction produces copolymers predominately of the following formula:

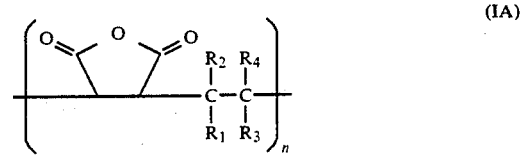

(IA)

wherein n is about 1 to about 100, preferably about 2 to about 20, more preferably 2 to 10, and R$_1$, R$_2$, R$_3$ and R$_4$ are selected from hydrogen, lower alkyl of about 1 to 6 carbon atoms and higher molecular weight polyalkyl, wherein either R$_1$ and R$_2$ are hydrogen and one of R$_3$ and R$_4$ is lower alkyl and the other is high molecular weight polyalkyl or R$_3$ and R$_4$ are hydrogen and one of R$_1$ and R$_2$ is lower alkyl and the other is high molecular weight polyalkyl.

Preferably, the high molecular weight polyalkyl group has at least about 30 carbon atoms (preferably at least about 50 carbon atoms). Preferred high molecular weight polyalkyl groups include polyisobutyl groups. Preferred polyisobutyl groups include those having average molecular weights of about 500 to about 5000, more preferably from about 900 to about 2500. Preferred lower alkyl groups include methyl and ethyl; especially preferred lower alkyl groups include methyl.

Generally, such copolymers contain an initiator group, I, and a terminator group, T, as a result of the reaction with the free radical initiator used in the polymerization reaction. In such a case, the initiator and terminator groups may be

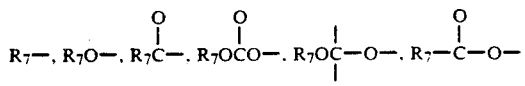

where $R_7$ is hydrogen, alkyl, aryl, alkaryl, cycloalkyl, alkoxy, cycloalkoxy, acyl, alkenyl, cycloalkenyl, alkynyl; or alkyl, aryl or alkaryl optionally substituted with 1 to 4 substituents independently selected from nitrile, keto, halogen, nitro, alkyl, aryl, and the like. Alternatively, the initiator group and/or terminator group may be derived from the reaction product of the initiator with another material such as solvent; for example, the initiator may react with toluene to produce a benzyl radical.

The copolymers of the present invention differ from the PIBSAs prepared by the thermal process in that the thermal process products contain a double bond and a singly substituted succinic anhydride group. The copolymers of the present invention differ from the PIBSAs prepared by the chlorination process, since those products contain a double bond, a ring, other than a succinic anhydride ring or one or more chlorine atoms.

The copolymers of the present invention contain no double bonds, rings, other than succinic anhydride rings, or chlorine atoms. In addition, the succinic anhydride groups are doubly substituted (i.e., have two substituents, one of which may be hydrogen) at the 2- and 3-positions, that is:

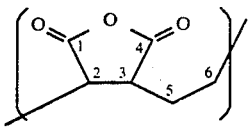

A(1) High Molecular Weight Polyalkylene Group

The high molecular weight polyalkyl group is derived from a high molecular weight olefin. The high molecular weight olefins used in the preparation of the copolymers of the present invention are of sufficiently long chain length so that the resulting composition is soluble in and compatible with mineral oils, fuels and the like; and the alkylvinylidene isomer of the high molecular weight olefin comprises at least about 20% of the total olefin composition.

Such high molecular weight olefins are generally mixtures of molecules having different molecular weights and can have at least one branch per 6 carbon atoms along the chain, preferably at least one branch per 4 carbon atoms along the chain, and particularly preferred that there be about one branch per 2 carbon atoms along the chain. These branched chain olefins may conveniently comprise polyalkenes prepared by the polymerization of olefins of from 3 to 6 carbon atoms, and preferably from olefins of from 3 to 4 carbon atoms, and more preferably from propylene or isobutylene. The addition-polymerizable olefins employed are normally 1-olefins. The branch may be of from 1 to 4 carbon atoms, more usually of from 1 to 2 carbon atoms and preferably methyl.

The preferred alkylvinylidene isomer comprises a methyl- or ethylvinylidene isomer, more preferably the methylvinylidene isomer.

The especially preferred high molecular weight olefins used to prepare the copolymers of the present invention are polyisobutenes which comprise at least about 20% of the more reactive methylvinylidene isomer, preferably at least 50% and more preferably at least 70%. Suitable polyisobutenes include those prepared using $BF_3$ catalysis. The preparation of such polyisobutenes in which the methylvinylidene isomer comprises a high percentage of the total composition is described in U.S. Pat. Nos. 4,152,499 and 4,605,808.

Polyisobutenes produced by conventional $AlCl_3$ catalysis when reacted with unsaturated acidic reactants, such as maleic anhydride, in the presence of a free radical initiator, produce products similar to thermal PIBSA in molecular weight and thus do not produce a copolymeric product.

Preferred are polyisobutenes having average molecular weights of about 500 to about 5000. Especially preferred are those having average molecular weights of about 900 to about 2500.

A(2) Unsaturated Acidic Reactant

The unsaturated acidic reactant used in the preparation of the copolymers of the present invention comprises a maleic or fumaric reactant of the general formula:

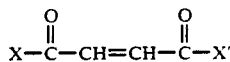

wherein X and X' are the same or different, provided that at least one of X and X' is a group that is capable of reacting to esterify alcohols, form amides or amine salts with ammonia or amines, form metal salts with reactive metals or basically reacting metal compounds and otherwise function to acylate. Typically, X and/or X' is —OH, —O—hydrocarbyl, —OM+ where M+ represents one equivalent of a metal, ammonium or amine cation, —$NH_2$, —Cl, —Br, and taken together X and X— can be —O— so as to form an anhydride. Preferably, X and X' are such that both carboxylic functions can enter into acylation reactions. Preferred are acidic reactants where X and X' are each independently selected from the group consisting of —OH, —Cl, —O—lower alkyl and when taken together, X and X' are —O—. Maleic anhydride is the preferred acidic reactant. Other suitable acidic reactants include electron-deficient olefins such as monophenyl maleic anhydride; monomethyl, dimethyl, monochloro, monobromo, monofluoro, dichloro and difluoro maleic anhydride; N-phenyl maleimide and other substituted maleimides; isomaleimides; fumaric acid, maleic acid, alkyl hydrogen maleates and fumarates, dialkyl fumarates and maleates, fumaronilic acids and maleanic acids; and maleonitrile, and fumaronitrile.

Preferred unsaturated acidic reactants include maleic anhydride, and maleic acid. The particularly preferred acidic reactant is maleic anhydride.

A(3) General Preparation of Copolymer

As noted above, the copolymers of the present invention are prepared by reacting a reactive high molecular weight olefin and an unsaturated acidic reactant in the presence of a free radical initiator.

The reaction may be conducted at a temperature of about −30° C. to about 210° C., preferably from about 40° C. to about 150° C. I have found that degree of polymerization is inversely proportional to temperature. Accordingly, for the preferred high molecular weight copolymers, it is advantageous to employ lower reaction temperatures. For example, if the reaction is conducted at about 138° C., an average degree of polymerization of about 1.3 was obtained. However, if the reaction was conducted at a temperature of about 40° C., an average degree of polymerization of about 10.5 was obtained.

The reaction may be conducted neat, that is, both the high molecular weight olefin, and acidic reactant and the free radical initiator are combined in the proper ratio, and then stirred at the reaction temperature.

Alternatively, the reaction may be conducted in a diluent. For example, the reactants may be combined in a solvent. Suitable solvents include those in which the reactants and free radical initiator are soluble and include acetone, tetrahydrofuran, chloroform, methylene chloride, dichloroethane, toluene, dioxane, chlorobenzene, xylenes, or the like. After the reaction is complete, volatile components may be stripped off. When a diluent is employed, it is preferably inert to the reactants and products formed and is generally used in an amount sufficient to ensure efficient stirring.

Moreover, my colleague W. R. Ruhe, has discovered that in the preparation of polyPIBSA, improved results are obtained by using PIBSA or polyPIBSA as a solvent for the reaction. (See, e.g., Examples 16, 17A and 17B herein.)

In general, the copolymerization can be initiated by any free radical initiator. Such initiators are well known in the art. However, the choice of free radical initiator may be influenced by the reaction temperature employed.

The preferred free-radical initiators are the peroxide-type polymerization initiators and the azo-type polymerization initiators. Radiation can also be used to initiate the reaction, if desired.

The peroxide-type free-radical initiator can be organic or inorganic, the organic having the general formula: $R_3OOR_3'$ where $R_3$ is any organic radical and $R_3'$ is selected from the group consisting of hydrogen and any organic radical. Both $R_3$ and $R_3'$ can be organic radicals, preferably hydrocarbon, aroyl, and acyl radicals, carrying, if desired, substituents such as halogens, etc. Preferred peroxides include di-tert-butyl peroxide, tert-butyl peroxybenzoate, and dicumyl peroxide.

Examples of other suitable peroxides, which in no way are limiting, include benzoyl peroxide; lauroyl peroxide; other tertiary butyl peroxides; 2,4-dichlorobenzoyl peroxide; tertiary butyl hydroperoxide; cumene hydroperoxide; diacetyl peroxide; acetyl hydroperoxide; diethylperoxycarbonate; tertiary butyl perbenzoate; and the like.

The azo-type compounds, typified by alpha,alpha'-azobisisobutyronitrile, are also well-known free-radical promoting materials. These azo compounds can be defined as those having present in the molecule group —N=N wherein the balances are satisfied by organic radicals, at least one of which is preferably attached to a tertiary carbon. Other suitable azo compounds include, but are not limited to, p-bromobenzenediazonium fluoborate; p-tolyldiazoaminobenzene; p-bromobenzenediazonium hydroxide; azomethane and phenyldiazonium halides. A suitable list of azo-type compounds can be found in U.S. Pat. No. 2,551,813, issued May 8, 1951 to Paul Pinkney.

The amount of initiator to employ, exclusive of radiation, of course, depends to a large extent on the particular initiator chose, the high molecular olefin used and the reaction conditions. The initiator must, of course, be soluble in the reaction medium. The usual concentrations of initiator are between 0.001:1 and 0.2:1 moles of initiator per mole of acidic reactant, with preferred amounts between 0.005:1 and 0.10:1.

The polymerization temperature must be sufficiently high to break down the initiator to produce the desired free-radicals. For example, using benzoyl peroxide as the initiator, the reaction temperature can be between about 75° C. and about 90° C., preferably between about 80° C. and about 85° C. Higher and lower temperatures can be employed, a suitable broad range of temperatures being between about 20° C. and about 200° C., with preferred temperatures between about 50° C. and about 150° C.

The reaction pressure should be sufficient to maintain the solvent in the liquid phase. Pressures can therefore vary between about atmospheric and 100 psig or higher, but the preferred pressure is atmospheric.

The reaction time is usually sufficient to result in the substantially complete conversion of the acidic reactant and high molecular weight olefin to copolymer. The reaction time is suitable between one and 24 hours, with preferred reaction times between two and ten hours.

As noted above, the subject reaction is a solution-type polymerization reaction. The high molecular weight olefin, acidic reactant, solvent and initiator can be brought together in any suitable manner. The important factors are intimate contact of the high molecular weight olefin and acidic reactant in the presence of a free-radical producing material. The reaction, for example, can be conducted in a batch system where the high molecular weight olefin is added all initially to a mixture of acidic reactant, initiator and solvent or the high molecular weight olefin can be added intermittently or continuously to the reaction pot. Alternatively, the reactants may be combined in other orders; for example, acidic reactant and initiator may be added to high molecular weight olefin and solvent in the reaction pot. In another manner, the components in the reaction mixture can be added continuously to a stirred reactor with continuous removal of a portion of the product to a recovery train or to other reactors in series. The reaction can also suitably take place in a coil-type reactor where the components are added at one or more points along the coil.

In one envisioned embodiment, the reaction product of an unsaturated acidic reactant and a high molecular weight, high vinylidene-containing olefin is further reacted thermally. In this embodiment, any unreacted olefin, generally the more hindered olefins, i.e., the non-vinylidene, that do not react readily with the unsaturated acidic reactant under free radical conditions are reacted with unsaturated acidic reactant under thermal conditions, i.e., at temperatures of about 180° to 280° C. These conditions are similar to those used for preparing thermal process PIBSA.

The reaction solvent, as noted above, must be one which dissolves both the acidic reactant and the high molecular weight olefin. It is necessary to dissolve the acidic reactant and high molecular weight olefin so as to bring them into intimate contact in the solution polymerization reaction. It has been found that the solvent must also be one in which the resultant copolymers are soluble.

Suitable solvents include liquid saturated or aromatic hydrocarbons having from six to 20 carbon atoms; ketones having from three to five carbon atoms; and liquid saturated aliphatic dihalogenated hydrocarbons having from one to five carbon atoms per molecule, preferably from one to three carbon atoms per molecule. By "liquid" is meant liquid under the conditions of polymerization. In the dihalogenated hydrocarbons, the halogens are preferably on adjacent carbon atoms. By "halogen" is meant F, Cl and Br. The amount of solvent must be such that it can dissolve the acidic reactant and high molecular weight olefin in addition to the resulting copolymers. The volume ratio of solvent to high molecular weight olefin is suitably between 1:1 and 100:1 and is preferably between 1.5:1 and 4:1.

Suitable solvents include the ketones having from three to six carbon atoms and the saturated dichlorinated hydrocarbons having from one to five, more preferably one to three, carbon atoms.

Examples of suitable solvents include, but are not limited to:
1. ketones, such as: acetone; methylethylketone; diethylketone; and methylisobutylketone;
2. aromatic hydrocarbons, such as: benzene; xylene; and toluene;
3. saturated dihalogenated hydrocarbons, such as: dichloromethane; dibromomethane; 1-bromo-2-chloroethane; 1,1-dibromoethane; 1,1-dichloroethane; 1,2-dichloroethane; 1,3-dibromopropane; 1,2-dibromopropane; 1,2-dibromo-2-methylpropane; 1,2-dichloropropane; 1,1-dichloropropane; 1,3-dichloropropane; 1-bromo-2-chloropropane; 1,2-dichlorobutane; 1,5-dibromopentane; and 1,5-dichloropentane; or
4. mixtures of the above, such as: benzenemethylethylketone.

As noted previously, W. R. Ruhe has discovered that use of a mixture of copolymer and polyisobutene as a solvent results in improved yields and advantageously dissolves the acidic reactant when used as a reaction medium.

The copolymer is conveniently separated from solvent and unreacted acidic reactant by conventional procedures such as phase separation, solvent distillation, precipitation and the like. If desired, dispersing agents and/or cosolvents may be used during the reaction.

The isolated copolymer may then be reacted with a polyamine to form a polymeric succinimide. The preparation and characterization of such polysuccinimides and their treatment with other agents to give other dispersant compositions is described herein.

A(4) Preferred Copolymers

Preferred copolymers include those where an unsaturated acidic reactant, most preferably maleic anhydride, is copolymerized with a "reactive" polyisobutene, in which at least about 50 percent or more of the polyisobutene comprises the alkylvinylidene, more preferably, the methylvinylidene, isomer, to give a "polyPIBSA".

Preferred are polyPIBSAs wherein the polyisobutyl group has an average molecular weight of about 500 to about 5000, more preferably from about 950 to about 2500. Preferred are polyPIBSAs having an average degree of polymerization of about 1.1 to about 20, more preferably from about 1.5 to about 10.

B. POLYSUCCINIMIDES

The polyamino polysuccinimides of the present invention are prepared by reacting a copolymer of the present invention with a polyamine. Polysuccinimides which may be prepared include monopolysuccinimides (where a polyamine component reacts with one succinic group), bis-polysuccinimides (where a polyamine component reacts with a succinic group from each of two copolymer molecules), higher succinimides (where a polyamine component reacts with a succinic group from each of more than 2 copolymer molecules) or mixtures thereof. The polysuccinimide(s) produced may depend on the charge mole ratio of polyamine to succinic groups in the copolymer molecule and the particular polyamine used. Using a charge mole ratio of polyamine to succinic groups in copolymer of about 1.0, predominately monopolysuccinimide is obtained. Charge mole ratios of polyamine to succinic group in copolymer of about 1:2 may produce predominately bis-polysuccinimide. Higher polysuccinimides may be produced if there is branching in the polyamine so that it may react with a succinic group from each of greater than 2 copolymer molecules.

B(1) Preferred Copolymers

Preferred copolymers include polyPIBSAs prepared according to the present invention as described hereinabove.

Preferred polyPIBSAs include those prepared using a polyisobutene of average molecular weight of about 500 to about 5000, preferably of about 950 to about 2500 and wherein at least about 50 percent of the total polyisobutene comprises the alkylvinylidene isomer. Preferred alkylvinylidene isomers include methylvinylidene and ethylvinylidene. Especially preferred is methylvinylidene. Preferred are polyPIBSAs having an average degree of polymerization of about 1.1 to about 15. Particularly preferred polyPIBSAs have an average degree of polymerization of about 1.5 to about 10, and which are prepared using a polyisobutene having an average molecular weight of about 900 to about 2500.

B(2) Polyamine

The polyamine employed to prepare the polyamino polysuccinimides is preferably polyamine having from 2 to about 12 amine nitrogen atoms and from 2 to about 40 carbon atoms. The polyamine is reacted with polyPIBSA to produce the polyamino polysuccinimide, employed in this invention. The polyamine is so selected so as to provide at least one basic amine per succinimide group. Since the reaction of a nitrogen of a polyamino polysuccinimide to form a hydrocarbyl oxycarbonyl, a hydroxy hydrocarbyl oxycarbonyl or a hydroxy polyoxyalkylene oxycarbonyl is believed to efficiently proceed through a secondary or primary amine, at least one of the basic amine atoms of the polyamino polysuccinimide must either be a primary amine or a secondary amine. Accordingly, in those instances in which the succinimide group contains only one basic amine, that amine must either be a primary amine or a secondary amine. The polyamine preferably has a carbon-to-nitrogen ratio of from about 1:1 to about 10:1.

The polyamine portion of the polyamino polysuccinimide may be substituted with substituents selected from (a) hydrogen, (b) hydrocarbyl groups of from 1 to about 10 carbon atoms, (c) acyl groups of from 2 to about 10 carbon atoms, and (d) monoketo, monohydroxy, mononitro, monocyano, lower alkyl and lower alkoxy derivatives of (b) and (c). "Lower", as used in terms like "lower alkyl" or "lower alkoxy", means a group containing from 1 to about 6 carbon atoms. At least one of the substituents on one of the amines of the polyamine is hydrogen, e.g., at least one of the basic nitrogen atoms of the polyamine is a primary or secondary amino nitrogen atom.

Hydrocarbyl, as used in describing the polyamine components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxyisopropyl, 4-hydroxybutyl, etc. ketoalkyls, such as 2-ketopropyl, 6-ketooctyl, etc., alkoxy and lower alkenoxy alkyls, such as ethoxyethyl, ethoxypropyl, propoxyethyl, propoxypropyl, 2-(2-ethoxyethoxy)ethyl, 2-(2-(2-ethoxy-ethoxy)ethoxy)ethyl, 3,6,9,12-tetraoxatetradecyl, 2-(2-ethoxyethoxy)hexyl, etc. The acyl groups of the aforementioned (c) substituents are such as propionyl, acetyl, etc. The more preferred substituents are hydrogen, $C_1$-$C_6$ alkyls and $C_1$-$C_6$ hydroxyalkyls.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and polysubstituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethylpropylene, trimethylene, etc. Examples of such polyamines include ethylene diamine, diethylene triamine, di(trimethylene)triamine, dipropylene triamine, triethylene tetramine, tripropylene tetramine, tetraethylene pentamine, and pentaethylene hexamine. Such amines encompass isomers such as branched-chain polyamine and the previously mentioned substituted polyamines, including hydrocarbyl-substituted polyamines. Among the polyalkylene polyamines, those containing 2-12 amine nitrogen atoms and 2-24 carbon atoms are especially preferred, and the $C_2$-$C_5$ alkylene polyamines are most preferred, in particular, the lower polyalkylene polyamines, e.g., ethylene diamine, dipropylene triamine, etc.

Preferred polyamines also include heavy polyamines such as polyamine HPA available from Union Carbide.

The polyamine component also may contain heterocyclic polyamines, heterocyclic substituted amines and substituted heterocyclic compounds, wherein the heterocycle comprises one or more 5 to 6-membered rings containing oxygen and/or nitrogen. Such heterocycles may be saturated or unsaturated and substituted with groups selected from the aforementioned (a), (b), (c) and (d). The heterocycles are exemplified by piperazines, such as 2-methylpiperazine, N-(2-hydroxyethyl)-piperazine, 1,2-bis-(n-piperazinyl)ethane, and N,N'-bis(N-piperazinyl)piperazine, 2-methylimidazoline, 3-aminopiperidine, 2-aminopyridine, 2-(3-aminoethyl)-3-pyrroline, 3-aminopyrrolidine, N-(3-aminopropyl)-morpholine, etc. Among the heterocyclic compounds, the piperazines are preferred.

Typical polyamines that can be used to form the compounds of this invention include the following: ethylene diamine, 1,2-propylene diamine, 1,3-propylene diamine, diethylene triamine, triethylene tetramine, hexamethylene diamine, tetraethylene pentamine, methylaminopropylene diamine, N-(betaaminoethyl)piperazine, N,N'-di(betaaminoethyl)piperazine, N,N'-di(-beta-aminoethyl)-imidazolidone-2, N-(beta-cyanoethyl)ethane-1,2-diamine, 1,3,6,9-tetraaminooctadecane, 1,3,6-triamino-9-oxadecane, N-(beta-aminoethyl)diethanolamine, N-methyl-1,2-propanediamine, 2-(2-aminoethylamino)-ethanol,2-[2-(2-aminoethylamino)ethylamino]-ethanol.

Another group of suitable polyamines are the propyleneamines, (bisaminopropylethylenediamines). Propyleneamines are prepared by the reaction of acrylonitrile with an ethyleneamine, for example, an ethyleneamine having the formula $H_2N(CH_2CH_2NH)_jH$ wherein $j$ is an integer from 1 to 5, followed by hydrogenation of the resultant intermediate. Thus, the product prepared from ethylene diamine and acrylonitrile would be $H_2N(CH_2)_3NH(CH_2)_2NH(CH_2)_3NH_2$.

In many instances the polyamine used as a reactant in the production of polysuccinimides of the present invention is not a single compound but a mixture in which one or several compounds predominate with the average composition indicated. For example, tetraethylene pentamine prepared by the polymerization of aziridine or the reaction of dichloroethylene and ammonia will have both lower and higher amine members, e.g., triethylene tetramine, substituted piperazines and pentaethylene hexamine, but the composition will be largely tetraethylene pentamine and the empirical formula of the total amine composition will closely approximate that of tetraethylene pentamine. Finally, in preparing the polysuccinimide for use in this invention, where the various nitrogen atoms of the polyamine are not geometrically equivalent, several substitutional isomers are possible and are encompassed within the final product. Methods of preparation of polyamines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99-116.

B(3) General Preparation

The polysuccinimides are prepared by reacting copolymer with a polyamine to form a mono-, bis-polysuccinimide, higher polysuccinimide or mixtures thereof. The charge mole ratio of polyamine to succinic groups in copolymer may determine the mixture of polysuccinimides formed. For example, a product comprising mono-, bis-polysuccinimide or higher polysuccinimide can be prepared by controlling the molar ratios of the polyamine and succinic groups in copolymer and the polyamine used. Thus, if about one mole of polyamine is reacted with one mole of succinic group in the copolymer, a predominately mono-polysuccinimide product will be prepared. If about two moles of succinic group in the copolymer are reacted per mole of polyamine, a bis-polysuccinimide may be prepared. If higher amounts of succinic group in copolymer are used, higher polysuccinimides may be prepared provided that there are sufficient basic amino groups (or sufficient branching) in the polyamine to react with a succinic group from each of several copolymer molecules to produce the higher polysuccinimide. Due to the cross-linking of copolymer molecules by the polyamine component, compositions of very high molecular weight, on the order of about 10,000 to about 100,000 may be prepared.

The reaction of a polyamine with an alkenyl or alkyl succinic anhydride to produce the polyamino alkenyl or alkyl succinimides is well known in the art and is disclosed in U.S. Pat. Nos. 2,992,708; 3,018,291; 3,024,237; 3,100,673; 3,219,666; 3,172,892; and 3,272,746. The above are incorporated herein by reference for their disclosures of preparing alkenyl or alkyl succinimides. The present polysuccinimides may be prepared by following the general procedures described therein.

Accordingly, polyamine and copolymer are contacted at the desired molar ratio to give the desired mono-, bispolysuccinimides or higher polysuccinimides or mixtures thereof. The reaction may be carried out neat or preferably in solution. Suitable solvents include organic solvents, including alcohols, aliphatic and aromatic solvents, and the like. The reaction is conducted at a temperature of about 80° C. to about 250° C., preferably from about 120° C. to about 180° C. and is generally complete within about 2 to about 24 hours. The reaction may be conducted under ambient pressure and atmospheric conditions, although a nitrogen atmosphere at atmospheric pressure may be preferred. The desired product may be isolated by conventional procedures, such as water wash and stripping, usually with the aid of vacuum, of any residual solvent.

B(4) General Preparation of Preferred Polysuccinimides

The preferred polysuccinimides of the present invention are prepared by reacting a polyPIBSA copolymer of the present invention with polyamine. The charge mole ratio of polyamine to succinic groups in the polyPIBSA will effect whether monopolysuccinimides, bis-polysuccinimides, or higher polysuccinimides or mixtures thereof are produced and/or predominate. Accordingly, with a charge mole ratio (CMR) of about one mole of polyamine per mole of succinic groups in the polyPIBSA primarily mono-polysuccinimide will be formed. However, at a CMR of 0.5 mole polyamine per mole of succinic group in the polyPIBSA, there is a tendency to form bis-polysuccinimides where the polyamine component acts to link two succinic groups, thusly forming a cross-linked composition. Accordingly, the reaction of polyPIBSA and polyamine will yield a mixture of products which I term "polysuccinimides" and which term includes monopolysuccinimides, also higher succinimides and bis-polysuccinimides and compositions of intermediate structure.

The reaction is carried out by contacting polyamine and polyPIBSA. Although the ratio of the reactants is not critical, as noted above a CMR may be chosen so as to yield desired polysuccinimide proportions. The reaction is carried out at a temperature sufficient to cause reaction of the polyamine with a succinic group of the polyPIBSA. In particular, reaction temperatures from about 120° C. to about 180° C. are preferred, with temperatures from about 140° C. to about 170° C. being especially preferred.

The reaction may be conducted neat—that is both the polyamine and the polyPIBSA are combined and then stirred at the reaction temperature.

Alternatively, the reaction may be conducted in a diluent. For example, the reactants may be combined in a solvent such as aliphatic or aromatic solvents, and the like, and then stirred at the reaction temperature. After completion of the reaction, volatile components may be stripped off. When a diluent is employed, it is preferably inert to the reactants and products formed and is generally used in an amount sufficient to ensure efficient stirring.

Preferred are polyamines having from about 2 to about 12 amine nitrogen atoms and from about 2 to about 40 carbon atoms. The more preferred polyamines employed in this reaction are generally represented by the formula:

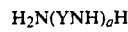

$$H_2N(YNH)_aH$$

wherein Y is an alkylene group of 2 to 10 carbon atoms, preferably from 2 to 6 carbon atoms, and a is an integer from about 1 to 11, preferably from 1 to 6. However, the preparation of these alkylene polyamines does not produce a single compound and cyclic heterocycles, such as piperazine, may be included to some extent in the alkylene diamines.

B(5) Preferred Polysuccinimides

(a) Monopolysuccinimides

Preferred monopolysuccinimides include those having the following formula:

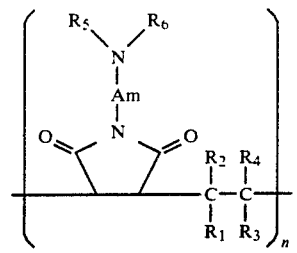

wherein Am is a linking group having from about 0 to about 10 amine nitrogen atoms and from about 2 to about 40 carbon atoms; n is 1 or greater and $R_1$, $R_2$, $R_3$ and $R_4$ are selected from hydrogen lower alkyl of 1 to 6 carbon atoms; and high molecular weight polyalkyl; wherein either $R_1$ and $R_2$ are hydrogen and one of $R_3$ and $R_4$ is lower alkyl and the other is high molecular weight polyalkyl or $R_3$ and $R_4$ are hydrogen and one of $R_1$ and $R_2$ is lower alkyl and the other is high molecular weight polyalkyl; and $R_5$ and $R_6$ are independently hydrogen, lower alkyl of 1 to 6 carbon atoms, phenyl or taken together are alkylene of 3 to 6 carbon atoms to give a ring.

Preferred high molecular weight polyalkyl groups include polyisobutyl groups having at least about 30 carbon atoms, more preferably, at least about 50 carbon atoms. Especially preferred are polyisobutyl groups having an average molecular weight of about 500 to about 5000, more preferably from about 900 to about 2500.

Preferred lower alkyl groups include methyl and ethyl. Especially preferred are compounds where the lower alkyl group is methyl.

Preferred are compounds where $R_5$ and $R_6$ are hydrogen or methyl; preferred $R_5$ and $R_6$ groups include hydrogen.

Preferred are Am groups having from about 0 to about 10 amine nitrogen atoms and from about 2 to about 40 carbon atoms. More preferred are Am groups of the formula —$[(ZNH)_p)Z']$—wherein Z and Z' are independently alkylene of from about 2 to about 6 carbon atoms and p is an integer from 1 to 6. Especially preferred are Am groups where Z and Z' are ethylene and p is 2, 3 or 4.

Preferred are compounds where n is from about 2 to about 20, more preferably from about 2 to about 10.

Preferred are compounds having an average degree of polymerization of from about 1.1 to about 20, more preferably from about 1.5 to about 10.

(b) Bis-polysuccinimides

Preferred polysuccinimides include those which partially comprise at least in part a bis-polysuccinimide structure. Some of these preferred polysuccinimides are random polysuccinimides which comprise units selected from:

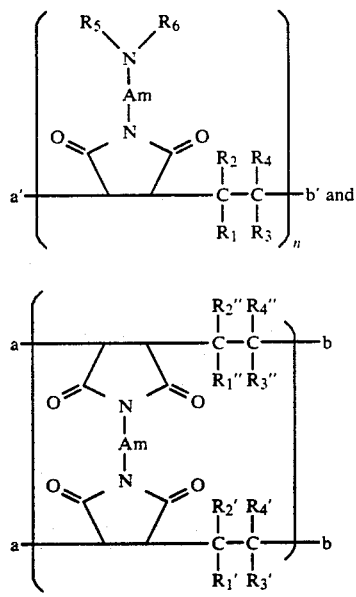

wherein Am is a linking group having from about 0 to 10 amine nitrogen atoms and from about 2 to 40 carbon atoms; $R_1$, $R_2$, $R_3$, $R_4$, $R_1'$, $R_2'$, $R_3'$, $R_4'$, $R_1''$, $R_2''$, $R_3''$, and $R_4''$ are selected from hydrogen, lower alkyl of one to 6 carbon atoms and high molecular weight polyalkyl; wherein either $R_1$ and $R_2$ are hydrogen and one of $R_3$ and $R_4$ is lower alkyl and the other is polyalkyl, or $R_3$ and $R_4$ are hydrogen and one of $R_1$ and $R_2$ is lower alkyl and the other is polyalkyl; either $R_1'$ and $R_2'$ are hydrogen and one of $R_3'$ and $R_4'$ is lower alkyl and the other is polyalkyl, or $R_3'$ and $R_4'$ are hydrogen and one of $R_1'$ and $R_2'$ is lower alkyl and the other is polyalkyl; and either $R_1''$ and $R_2''$ are hydrogen and one of $R_3''$ and $R_4''$ is lower alkyl and the other is polyalkyl or $R_3''$ and $R_4''$ are hydrogen and one of $R_1''$ and $R_2''$ is lower alkyl and the other is polyalkyl and $R_5$ and $R_6$ are independently hydrogen, lower alkyl of 1 to 6 carbon atoms, phenyl or taken together are alkylene of 3 to 6 carbon atoms to give a ring; a, a', b and b' are sites for a covalent bond provided that at least one a or a' site of each unit is covalently bonded to a b or b' site.

Preferred polyalkyl groups include polyisobutyl groups having at least about 30 carbon atoms, more preferably at least about 50 carbon atoms. Especially preferred are polyisobutyl groups having an average molecular weight of about 500 to about 5000, more preferably from about 900 to about 2500.

Preferred lower alkyl groups include methyl and ethyl; especially preferred is ethyl.

Preferred Am groups include those having the formula —$[ZNH)pZ']$— wherein Z and Z' are independently alkylene of 2 to 6 carbon atoms and p is an integer from 0 to 5. Especially preferred are Am groups wherein Z and Z' are ethylene and p is 1, 2 or 3.

Preferred are random polysuccinimides where the average sum of A and B units is from about 2 to about 50. preferred are random polysuccinimides having molecular weights of from about 10,000 to about 150,000.

Preferred are compounds in which the bis-succinimide structure predominates, that is those having more B units than A units, preferably on the order of about 2 to about 10 times as many B units as A units. Such compounds are preferred in part due to their high average molecular weights, on the order of about 10,000 to about 150,000 which may be related to their exhibiting an advantageous V.I. credit as well as dispersantability when used in a lubricating oil composition.

It is believed that polysuccinimide compounds in which a significant portion comprises a bis-polysuccinimide structure (an embodiment which is exemplified in FIG. 1) comprise network or ladder polymers. Such polymers are cross-linked in an orderly manner. It is believed that this orderly cross-linking allows for the formation of compositions having very high molecular weights, on the order of about 10,000 to about 150,000 and also contributes to the advantageous properties of these compositions including improved dispersancy and V.I. credit. In addition, due to the cross-linking of the copolymer molecules by the polyamine to form the polysuccinimides of the above-noted structure, such products are harder to hydrolyze and are more stable to shear forces than are those polysuccinimides which do not form the ladder structure.

(c) Higher Polysuccinimides

Higher polysuccinimides are prepared by reacting the copolymers of the present invention with a polyamine having branching such that it can react with a succinic group from each of greater than two copolymer molecules. Due to this crosslinking, it is believed that these higher polysuccinimides may have gel-like properties besides the dispersant properties possessed by the other polysuccinimides.

C. POLYAMINO POLYSUCCINIMIDES WHEREIN ONE OR MORE OF THE NITROGENS IS SUBSTITUTED WITH HYDROCARBYL OXYCARBONYL, HYDROXY HYDROCARBYL OXYCARBONYL, OR HYDROXY POLY(OXYALKYLENE)OXYCARBONYL) OR THE POLYSUCCINIMIDE IS OTHERWISE POST-TREATED

Commonly-assigned U.S. Pat. No. 4,612,132 discloses polyamino alkenyl or alkyl succinimides wherein one or more of the nitrogens of the polyamino moiety is substituted with a hydrocarbyl oxycarbonyl, or a hydroxy hydrocarbyl oxycarbonyl wherein said hydrocarbyl contains from 1 to about 20 carbon atoms and said hydroxy hydrocarbyl contains from about 2 to about 20 carbon atoms which may be prepared by reaction with a cyclic carbonate; by reaction with a linear mono- or polycarbonate; or by reaction with a suitable chloroformate and hydroxy poly(oxyalkylene)oxycarbonyl which may be formed by reaction with a suitable chloroformate. U.S. Pat. No. 4,612,132 also discloses processes for the preparation of such modified polyamino alkenyl or alkyl succinimides.

U.S. Pat. No. 4,612,132 also discloses the post-treating of hydroxyhydrocarbyl carbamates prepared from polyamino alkenyl or alkyl succinimides with an alkenyl or alkyl succinic anhydride.

In addition, U.S. Pat. No. 4,612,132 discloses the reaction of the modified succinimides disclosed therein with boric acid or similar boron compound to give borated dispersants. Accordingly, the disclosure of U.S. Pat. No. 4,612,132 is incorporated herein by reference.

Commonly assigned U.S. Pat. No. 4,585,566 discloses improved dispersants prepared by reacting other nitrogen-containing dispersants with cyclic carbonates, the disclosure of which is incorporated herein by reference.

Accordingly, by following the procedures disclosed in U.S. Pat. Nos. 4,612,132 and 4,585,566, modified polysuccinimides may be prepared. Thus, the polyamino polysuccinimides wherein one or more of the nitrogens of the polyamino moiety is substituted with a hydrocarbyl oxycarbonyl, or a hydroxy hydrocarbyl oxycarbonyl wherein said hydrocarbyl contains from 1 to about 20 carbon atoms and said hydroxy hydrocarbyl contains from 2 to about 20 carbon atoms may be prepared by reaction with a cyclic carbonate; by reaction with a linear mono- or poly-carbonate; or by reaction with a suitable chloroformate. Hydroxy poly(oxyalkylene) oxycarbonyl may be formed by reaction with a suitable chloroformate. Also, hydroxy hydrocarbyl carbamates prepared from the polysuccinimides of the present invention may be post-treated with an alkenyl or alkyl succinic anhydride [or even the copolymers of the present invention (such as polyPIBSA) according to the procedures disclosed in U.S. Pat. Nos. 4,612,132 and 4,585,566. The products so produced are effective dispersant and detergent additives for lubricating oils and for fuel.

The polysuccinimides and modified polysuccinimides of this invention can also be reacted with boric acid or a similar boron compound to form borated dispersants having utility within the scope of this invention. In addition to boric acid (boron acid), examples of suitable boron compounds include boron oxides, boron halides and esters of boric acid. Generally from about 0.1 equivalents to 10 equivalents of boron compound to the polysuccinimide or modified polysuccinimide may be employed.

Commonly-assigned U.S. Pat. No. 4,615,826 discloses the treating of a succinimide having at least one basic nitrogen with a fluorophosphoric acid or ammonium salt thereof to give a hydrocarbon-soluble fluorophosphoric acid adduct. Accordingly, the disclosure of U.S. Pat. No. 4,615,826 is incorporated herein by reference.

By following the disclosure of U.S. Pat. No. 4,615,826, hydrocarbon-soluble fluorophosphoric adducts of the polysuccinimides of the present invention may be prepared. Such adducts comprise the reaction product of a polysuccinimide of the present invention and a fluorophosphoric acid or ammonium salt thereof wherein the amount of said fluorophosphoric acid or salt thereof is from about 0.1 to about 1 equivalent per equivalent of basic nitrogen atom.

The copolymers of the present invention, including preferred copolymers such as polyPIBSA may be post-treated with a wide variety of other post-treating reagents. U.S. Pat. No. 4,234,435, the disclosure of which is incorporated herein by reference, discloses reacting succinic acylating agents with a variety of reagents to give post-treated carboxylic acid derivative compositions which are useful in lubricating oil compositions.

D. LUBRICATING OIL COMPOSITIONS

The copolymers, polysuccinimides and modified polysuccinimides of this invention are useful as detergent and dispersant additives when employed in lubricating oils. When employed in this manner, the additives of the present invention are usually present in from 0.2 to 10 percent by weight to the total composition and preferably at about 0.5 to 8 percent by weight and more preferably at about 1 to about 6 percent by weight. The lubricating oil used with the additive compositions of this invention may be mineral oil or synthetic oils of lubricating viscosity and preferably suitable for use in the crankcase of an internal combustion engine. Crankcase lubricating oils ordinarily have a viscosity of about 1300 CSt 0° F. to 22.7 CSt at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity, such as didodecyl benzene, can be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Lubricating oil concentrates are also included within the scope of this invention. The concentrates of this invention usually include from about 90 to 10 weight percent, preferably from about 90 to about 50 weight percent, of an oil of lubricating viscosity and from about 10 to 90 weight percent, preferably from about 10 to about 50 weight percent, of an additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other well-known additives. It is also contemplated the additives of this invention may be employed as dispersants and detergents in hydraulic fluids, marine crankcase lubricants and the like. When so employed, the additive is added at from about 0.1 to 10 percent by weight to the oil. Preferably, at from 0.5 to 8 weight percent.

E. FUEL COMPOSITIONS

When used in fuels, the proper concentration of the additive necessary in order to achieve the desired detergency is dependent upon a variety of factors including the type of fuel used, the presence of other detergents or dispersants or other additives, etc. Generally, however, and in the preferred embodiment, the range of concentration of the additive in the base fuel is 10 to 10,000 weight parts per million, preferably from 30 to 5000 parts per million of the additive per part of base fuel. If other detergents are present, a lesser amount of the additive may be used. The additives of this invention may be formulated as a fuel concentrate, using an inert stable oleophilic organic solvent boiling in the range of about 150° to 400° F. Preferably, an aliphatic or an aromatic hydrocarbon solvent is used, such a benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the fuel additive. In the fuel concentrate, the amount of the additive will be ordinarily at least 5 percent by weight and generally not exceed 70 percent by weight, preferably from 5 to 50 and more preferably from 10 to 25 weight percent.

The following examples are offered to specifically illustrate this invention. These examples and illustrations are not to be construed in any way limiting the scope of this invention.

EXAMPLES

Example 1

Preparation of Polyisobutyl-24 PolyPIBSA

To a 12-liter, 3-neck flask equipped with an overhead stirrer, thermometer, condenser, and heating mantle under nitrogen atmosphere was added 5,000 grams (5.265 mole) of polyisobutene of about 950 molecular weight having the trade name ULTRAVIS-10 obtained from BP Chemicals wherein the methylvinylidene isomer comprised about 70% of the total composition, 1547.1 grams (15.79 mole) maleic anhydride, and 2,500 ml chloroform. The mixture was heated to reflux, and to this was added 67.21 grams (0.41 mole) 22'-azobis (2-methyl-propionitrite) ("AIBN"). The mixture was refluxed for two hours at which time an additional 67.21 grams of AIBN was added. This was followed by another two hours of reflux and a third charge (66.58 grams) of AIBN. A total of 201 grams (1.2 mole) of AIBN was added. The reaction mixture was refluxed a total of 20 hours, and then allowed to cool. Two layers formed. The lower phase which contained mostly chloroform and unreacted maleic anhydride was discarded. The upper layer which contained mainly product and unreacted polyisobutene was separated. Solvent and maleic anhydride were removed in vacuo. A total of 4,360 grams of product having a saponification number of 40.4 was recovered.

Example 2

Preparation of Polyisobutyl-24 PolyPIBSA

To a 1-liter 3-neck flask equipped with a thermometer, overhead stirrer, nitrogen inlet and water condenser, was added 165.02 grams (0.174 mole) polyisobutylene (ULTRAVIS-10 from BP Chemicals) and 105 ml dichloroethane, then 16.4 grams (0.167 mole) maleic anhydride were added. The resulting mixture was heated to about 45° C., and 3.3 grams (0.017 mole) tert-butylperbenzoate was added. The resulting mixture was heated to reflux (83° C.). The reaction mixture was heated (with stirring) for a total of 30 hours. The reaction mixture was allowed to cool. The solvent was removed in vacuo. Unreacted maleic anhydride was removed by heating the residue to 150° C. at 0.1 mm Hg vacuum. A total of 176.0 grams product was obtained, which had an average molecular weight of about 5000. The conversion was about 60%. The saponification number was 73.3.

Examples 3 to 15 and Comparison Examples 1C to 5C

Table I tabulates additional preparations following the basic synthetic procedure outlined in Examples 1 and 2. Table I lists the reactants, reaction temperature, time and solvent, and free radical initiator used.

Example 12 was prepared using polyisobutene of about 1300 molecular weight having the trade name ULTRAVIS-30 obtained from BP chemicals wherein the methylvinylidene isomer comprised about 70% of the total composition.

Comparison Examples 1C to 5C were prepared using a polyisobutylene of about 950 molecular weight prepared with AlCl$_3$ catalysis having the trade name Parapol 950 obtained from Exxon Chemical.

TABLE I

| Product of Example No. | Polybutene (g) | Maleic Anhydride (g) | Solvent (ml) | Initiator* (g) | Temp °C. | Time Hrs. |
|---|---|---|---|---|---|---|
| 2 | Ultravis-10 (165.09) | 16.4 | Dichloroethane (105) | TBPB (3.3) | 83 | 30 |
| 3 | Ultravis-10 (384.6) | 119 | Toluene (250) | AIBN (15.5) | 110 | 6 |
| 4 | Ultravis-10 (330) | 32.3 | Chlorobenzene (210) | DTBP (5.8) | 138 | 30 |
| 5 | Ultravis-10 (5000) | 1547 | Dichloroethane (2500) | AIBN (200) | 83 | 13 |

TABLE I-continued

| Product of Example No. | Polybutene (g) | Maleic Anhydride (g) | Solvent (ml) | Initiator* (g) | Temp °C. | Time Hrs. |
|---|---|---|---|---|---|---|
| 6 | Ultravis-10 (384.6) | 119 | Chloroform (250) | AIBN (15.5) | 74 | 24 |
| 7 | Ultravis-10 (384.6) | 119 | Methylene Chloride (250) | AIBN (15.5) | 40 | 94 |
| 8 | Ultravis-10 (330) | 32.3 | Toluene (210) | DTBP (5.8) | 110 | 30 |
| 9 | Ultravis-10 (330) | 32.3 | Xylene (210) | DTBP (5.8) | 144 | 39 |
| 10 | Ultravis-10 (330) | 32.3 | Xylene (210) | DTBP (5.8) | 114 | 4 |
| 11 | Ultravis-10 (330) | 32.3 | Toluene (210) | DTBP (5.8) | 110 | 4 |
| 12 | Ultravis-30 (217.1) | 16.4 | Dichloroethane (105) | TBPB (3.3) | 83–184 | 26 |
| 13 | Ultravis-10 (3350) | 328.3 | Chlorobenzene (1600) | DTBP (42.6) | 138 | 28 |
| 14 | Ultravis-10 (5000) | 515.8 | Chloroform (3000) | TBPB (102.8) | 72 | 54 |
| 15 | Ultravis-10 (10,000) | 1031 | Chloroform (6000) | TBPB (205.6) then | 72 140 | 48 2 |
| 1C | Parapol 950 (384.6) | 119 | Toluene (250) | AIBN (15.5) | 110 | 6 |
| 2C | Parapol 950 (76.4) | 23.8 | Dichloroethane (50) | AIBN (2.33) | 83 | 4 |
| 3C | Parapol 950 (330) | 32.3 | Toluene (210) | DTBP (5.8) | 110 | 30 |
| 4C | Parapol 950 (330) | 32.3 | Xylene (210) | DTBP (5.8) | 114 | 30 |
| 5C | Parapol 950 (330) | 32.3 | Chlorobenzene (210) | DTBP (5.8) | 138 | 30 |

*AIBN = 2,2'-azobis (2-methyl-propionitrile); DTBP = ditertbutyl peroxide; TBPB = tertbutyl peroxybenzoate
**Molecular weight 1300

Example 16

A 500-ml, 3-necked flask was charged with 100 g of a polyPIBSA polybutene mixture (prepared according to the method of Example 5) which comprised about 38 weight percent polyPIBSA and about 62 weight percent unreacted polyisobutene (of which about 68 weight percent comprised the methylvinylidene isomer). The mixture was heated to 70° C. Then, 8 g maleic anhydride and 1.7 g di-tert-butyl peroxide were added to the mixture. The mixture was stirred and heated to 150° C. for 5 hours. After allowing the mixture to cool, 150 ml hexane was added to precipitate unreacted maleic anhydride which was then removed by filtration. The hexane was removed by stripping for 4 hours at 36 mm Hg (abs) at 90° C. The product had a maleic anhydride content of 0.08 weight percent.

Example 17A

A 22-liter, 3-necked flask was charged with 3752 g of polyisobutene (BP Ultravis 10) and 2800 g of a poly-PIBSA polyisobutene mixture (prepared according to Example 13) which comprised about 57 weight percent polyPIBSA and about 43 weight percent unreacted polyisobutene). The mixture was heated to 91° C.; then 14 g maleic anhydride and 2.7 g di-tert-butyl peroxide (DTBP) were added. A slight exotherm was noticed where the temperature increased to 147° C. The mixture was stirred and heated at 140° C. for one hour. After standing at room temperature overnight, the mixture was heated to 140° C. and 378 g maleic anhydride and 56.7 g of DTBP were added. The mixture was stirred and heated at 140° C. for 6.5 hours. The mixture was allowed to cool to ambient temperature overnight. The mixture was heated to 80° C. and vacuum was applied at 28 inches Hg (vac); the temperature was increased to 200° C. The mixture was stripped at 200° C. and 28 inches Hg (vac) for 2 hours to remove unreacted maleic anhydride.

Example 17B

A 22-liter, 3-necked flask was charged with 8040 g polyisobutene (BP Ultravis 10) and 6000 g of a polyPIB-SA/polybutene mixture prepared according to Example 17A. The mixture was heated to 109° C., then 840 g maleic anhydride and 126 g DTBP were added. The resulting mixture was stirred and heated at 140° C. for 5.25 hours. The mixture was cooled to ambient temperature. The mixture was then heated to 128° C. with stirring and an additional 153 g maleic anhydride and 23 g DTBP were added. The mixture was stirred and heated at 140° C. for 3.5 hours and then an additional 153 g maleic anhydride and 11.8 g DTBP were added. The mixture was stirred and heated at 140° C. for an additional 3.67 hours. The mixture was cooled to ambient temperature. The mixture was then stirred and heated at 186° C. for one hour while vacuum was applied to strip the unreacted maleic anhydride from the product. The product had a saponification number of 85.8 mg KOH/g.

Example 18

Preparation of PolyPIBSA TETA-Polysuccinimide with a High Degree of Polymerization To a 12-liter flask equipped with a Dean Stark trap, overhead stirrer and heating mantle under nitrogen was added 4340 g polyPIBSA prepared according to Example 1 (saponification No. 40.4 mg KOH/g, molecular weight about 9000). The resulting mixture was heated to 130° C. with stirring, then 163.7 g (1.12 mole) triethylenetetraamine (TETA) were added. The reaction mixture was stirred overnight at 160° C. to 215° C.; 24 ml water were collected (in the Dean Stark trap) The reaction mixture was allowed to cool.

Obtained was 4360 g of a polysuccinimide of about 58,000 molecular weight having the following characteristics: 1.45% N, TAN 1.01, TBN 26.9, viscosity at 100° C. 2649 cSt. The molecular weight was determined using 1-1000Å and 1-500Å ultrastyrogel columns connected in series using 10% propylamine 90% THF as a solvent and comparing the retention time with known (molecular weight) polystyrene standards.

Example 19

Preparation PolyPIBSA TEPA Polysuccinimide With a High Degree of Polymerization

To a 3-neck one-liter flask equipped with heating mantle, overhead stirrer and Dean Stark trap, was added 213.4 g polyPIBSA prepared according to the method of Example 5 (molecular weight about 6000). The system was heated to 90° C. with stirring; then 18.98 g of tetraethylene pentaamine (TEPA) (0.1003 g). The resulting mixture was heated to 176° C. under nitrogen sweep. A small amount of water (about 0.5 ml) was removed. After 3.5 hours, the mixture was placed under vacuum and was heated under vacuum for 0.5 hours; the heating was then stopped. Obtained was 226.9 g of product, a polyPIBSA TEPA polysuccinimide.

21 Example 20

Preparation of PolyPIBSA TETA Polysuccinimide With a High Degree of Polymerization To a 12-liter flask equipped with an overhead stirrer, heating mantle and Dean Stark trap, under nitrogen sweep, was added 4539 g polyPIBSA prepared according to Example 5 (saponification number 36.3, molecular weight about 6600). The system was heated to 125° C. with stirring; then 131.6 g triethylene tetraamine (TETA) was added. The reaction mixture was heated to 165° C. for 5 hours. A total of 21.5 ml water was collected in the Dean Stark trap. The mixture was then heated under vacuum at 180° C. for two hours. The reaction mixture was allowed to cool. Obtained was 4589 g of product, a polysuccinimide of about 35,000 molecular weight having the following characteristics: % N 1.14, TAN 2.33, TBN 20.1, viscosity at 100° C. 1817 cSt.

Example 21

Preparation of PolyPIBSA TETA Polysuccinimide with a Low Degree of Polymerization To a 5-liter flask equipped with a heating mantle, overhead stirrer and Dean Stark trap under nitrogen sweep, was added 1000 g polyPIBSA prepared according to Example 17B (saponification number 85.8, molecular weight about 2500) and 999 g Chevron 100NR diluent oil. The mixture was heated to 60° C.; then 75.78 g TETA was added. The mixture was heated to 160° C. and kept at temperature for 4 hours. A total of 7.0 ml water was recovered from the Dean Stark trap. The reaction mixture was then maintained at 160° C. under vacuum for 2 hours. The reaction mixture was allowed to cool. Obtained was 2018.2 g of product having % N=1.35.

Example 22

Preparation of PolyPIBSA HPA Polysuccinimide With a Low Degree of Polymerization To a 5-liter flask equipped with a heating mantle, overhead stirrer and Dean Stark trap (under nitrogen sweep) was added 1000 g polyPIBSA prepared according to Example 17B (saponification number 85.8 molecular weight 2500) and 932 Chevron 100NR diluent oil. The mixture was heated to 60° C.; to this was added 142.45 g heavy polyamine ("HPA") No. X obtained from Union Carbide Corporation. The mixture became very thick. The reaction mixture was heated to 165° C. and maintained at that temperature for 4 hours; the mixture became less viscous. Then the reaction mixture was heated at 165° C. under vacuum for 2 hours. The mixture was allowed to cool. Obtained was the above-identified product having N=2.23.

Example A

Determination of Saponification Number

Saponification number was determined by using ASTM procedure D94-80.

Results for the products of Examples 2 to 15 and 1C to 5C are given in Table II.

Example B

Determination of Percent Unreacted Polyisobutylene and Percent Product

The percent of unreacted polyisobutylene and percent product were determined according to the following procedure.

A 5.0-gram sample of product was dissolved in hexane, placed in a column of 80.0-gram silica gel (Davisil 62,140Å pore size silica gel), and eluted with 600 ml hexane. The percent unreacted polybutylene was determined by removing the hexane solvent in vacuo (from the eluent) and weighing the residue. The silica gel from the column was removed and suspended in a 1-liter beaker with 250 ml dioxane. The mixture was heated to boiling, and the filtered. The process was repeated three more times. The dioxane solutions were combined and then stripped to dryness in vacuo and the percent product determined by weighing the residue. Results for the Products of Examples 2 to 15 and 1C to 5C are tabulated in Table II.

Example C

Determination of Molecular Weight of The PolyPIBSA Product and Degree of Polymerization The molecular weight of the product was determined according to the following procedure.

A 0.5% solution of product in tetrahydrofuran was injected onto two 500-Å gel permeation columns (ultrastyrogel) connected in series. The solvent used was 1 to 3 percent methanol in tetrahydrofuran. (The columns were eluted with a 1% or 3 percent solutions methanol in tetrahydrofuran.) Molecular weight was determined by comparison of retention times of the product to the retention times of polystyrene standards.

Degree of polymerization was calculated by dividing the molecular weight by 1,050 (the calculated average molecular weight of a monomer having one succinic group and one polyisobutylene group of average molecular weight of 952).

Results for the products of Examples 2 to 15 and 1C to 5C are tabulated in Table II.

Example D

Calculation of "PIBSA Number"

The PIBSA number was calculated by dividing the saponification number by the percent product. This gave the "PIBSA number" which is a saponification number for polyPIBSA on a 100% actives basis. This value is tabulated in Table III.

Calculated PIBSA numbers for the products of Examples 2 to 15 and 1C and 5C are tabulated in Table III.

It is believed that polyPIBSA comprises a copolymer having alternating succinic and polyisobutyl groups.

Example E

Fourier Transform Infrared Spectra of PolyPIBSA

The Fourier Transform Infrared (FTIR) Spectra (having a resolution of 2 $cm^{-1}$) of some of the polyPIBSA copolymers of the present invention and also some comparison compounds were recorded on a Nicolet MX-1 FTIR. Samples whose spectra was to be run were prepared by dissolving in Chevron 100NR mineral oil at a concentration of 5 percent by weight. The FTIR frequency for the anhydride stretch for each sample was measured and is recorded in Table IV.

As may be seen from Table IV, PIBSA prepared by the thermal process ("thermal PIBSA") prepared from (a) BP ultravis polyisobutene (having about 70% of the total composition in the methylvinylidene configuration) and (b) Exxon Parapol polyisobutene both exhibited the anhydride stretch frequency at 1793 $cm^{-1}$. PIBSA prepared according to the chlorination process ("Chlorination PIBSA") from the Exxon Parapol polyisobutene had an anhydride stretch frequency at 1785 $cm^{-1}$. In contrast, copolymers of the present invention comprising polyPIBSA (prepared according to Examples 3 to 12) exhibited anhydride stretch frequencies in the range of 1777 to 1783 $cm^{-1}$. Comparison Examples 1C to 5C which were prepared by reacting the Exxon Parapol polyisobutene (which did not comprise at least about 20 percent of the alkylvinylidene isomer) under free radical conditions exhibited anhydride stretch absorbences in the range of 1785 to 1790 $cm^{-1}$ the range for the conventional PIBSA materials. It is believed that these differences are due to the 2,3-disubstitution that is present in the one-to-one alternating copolymers of the present invention.

Example F

Fourier Transform Infrared Spectra of Polysuccinimides

The Fourier Transform Infrared (FTIR) spectra of some of the polysuccinimides of the present invention and also of some comparison compounds were recorded. Samples were prepared as described in Example E and the FTIR frequency for the succinimide stretch for each sample is recorded in Table V.

As may be seen from Table V, MS-Th, monosuccinimide prepared from Thermal PIBSA and BS-Th, bissuccinimide prepared from Thermal PIBSA exhibit the succinimide stretch at 1705.1 $cm^{-1}$ and 1707.0 $cm^{-1}$, respectively. MS-Cl monosuccinimide prepared from chlorination PIBSA, PS-Cl, a polysuccinimide prepared from chlorination PIBSA and CS-CL, a commercial succinimide prepared from chlorination PIBSA, exhibit succinimide stretches at 1706.2 $Cm^{-1}$, 1705.1 $cm^{-1}$ and 1705.1 $cm^{-1}$, respectively.

In contrast, the polysuccinimides of the present invention exhibit succinimide stretches between about 1697 $cm^{-1}$ and about 1703 $cm^{-1}$. It is believed that the characteristic frequency for the succinimide stretch is due to the disubstitution at the 2- and 3-positions in the polysuccinimide structure, similar to the characteristic anhydride stretch exhibited by the polyPIBSA copolymers.

Example G

Sequence VE Test - Sludge

Formulated oils containing a polysuccinimide of the present invention prepared according to Example 18 were tested according to the Sequence VE Engine Test Procedure (Sequence VE Test Procedure, Seventh Draft, May 19, 1988) and evaluated for sludge. The test formulations were compared with two industry reference oils: Reference A, a poor performing oil, and Reference B, a good performing oil. Sludge ratings of 9 or greater are advantageous and generally considered passing. Results are tabulated in Table VI.

TABLE II

| Product of Example | Weight Product, g | Saponification Value, mgKOH/g Sample | % Unreacted Polybutene | % Product | Molecular Wt. Product | Average Degree of Polymerization |
|---|---|---|---|---|---|---|
| 2 | 176 | 73.3 | 40 | 60 | 5,000 | 4.8 |
| 3 | 370 | N/A | 59 | 39 | 1,700 | 1.6 |
| 4 | 355 | 78.9 | 36 | 58 | 1,350 | 1.3 |
| 5 | 4,589 | 36.3 | 64 | 36 | 6,600 | 6.3 |
| 6 | 374 | 45.4 | 62 | 37 | 9,100 | 8.7 |
| 7 | 365 | 43.3 | 57 | 43 | 11,000 | 10.5 |
| 8 | 357 | 78.3 | 36 | 60 | 1,400 | 1.3 |
| 9 | 364 | 78.4 | 40 | 53 | 1,200 | 1.1 |
| 10 | 361 | 79.8 | 39 | 58 | 1,300 | 1.2 |
| 11 | 341 | 35.8 | 65 | 32 | 1,900 | 1.8 |
| 12 | 232 | 39.6 | 35 | 65 | 8,000 | 5.7 |
| 13 | 3,605 | 80.3 | 35 | 57 | 1,350 | 1.3 |
| 14 | 5,465 | N/A | 33 | 65 | 3,300 | 3.1 |
| 15 | 10,462 | N/A | 35 | 63 | 12,000 | 11.4 |
| 1C | 352 | 24.3 | 87 | 11 | 900 | 0.9 |
| 2C | 68 | N/A | N/A | N/A | N/A | N/A |
| 3C | 351 | 87.3 | 52 | 34 | 900 | 0.9 |
| 4C | 357 | 80.9 | 57 | 34 | 950 | 0.9 |
| 5C | 356 | N/A | 56 | 32 | 950 | 0.9 |

N/A = Not Available
Formed two phases = from upper phase only

TABLE III

| Product of Example | PIBSA Number of 100% Active Material* | Average Molecular Weight |
|---|---|---|
| 2 | 122 | 5,000 |
| 3 | N/A | 1,700 |
| 4 | 136 | 1,350 |
| 5 | 101 | 6,600 |
| 6 | 123 | 9,100 |
| 7 | 101 | 11,000 |
| 8 | 131 | 1,400 |
| 9 | 148 | 1,200 |
| 10 | 138 | 1,300 |
| 11 | 112 | 1,900 |
| 12 | 61 | 8,000 |
| 13 | 141 | 1,350 |
| 14 | N/A | 3,300 |
| 15 | N/A | 12,000 |
| 1C | 219 | 900 |
| 2C | N/A | N/A |
| 3C | 287 | 900 |
| 4C | 266 | 950 |
| 5C | 295 | 950 |

N/A = Not Available
*Includes base titration of benzoic acid initiator, where used.

TABLE IV

FTIR Spectra of PolyPIBSA

| Sample-Product of Example No. | Molecular Weight | FTIR Frequency (cm$^{-1}$) |
|---|---|---|
| 2 | 5,000 | 1779.7 |
| 3 | 1,700 | 1781.2 |
| 4 | 1,350 | 1782.8 |
| 5 | 6,600 | 1778.1 |
| 6 | 9,100 | 1777.3 |
| 7 | 11,000 | 1775.8 |
| 8 | 1,400 | 1781.2 |
| 9 | 1,200 | 1782.8 |
| 10 | 1,300 | 1782.8 |
| 11 | 1,900 | 1780.5 |
| 12 | 8,000 | 1778.1 |
| 13 | 1,350 | N/A |
| 1C | 900 | 1789.8 |
| 2C | N/A$^a$ | 1789.1 |
| 3C | 900 | 1785.2 |
| 4C | 950 | 1787.5 |
| 5C | 950 | 1785.9 |
| Thermal PIBSA (BP polyisobutene) | | 1793.0 |
| Thermal PIBSA (Exxon polyisobutene) | | 1793.0 |
| Chlorination PIBSA (Exxon polyisobutene) | | 1785. |
| Chlorination PIBSA (Commercial Product) | | 1785. |

$^a$N/A = not available.

TABLE V

FTIR Spectra of Polysuccinimides

| Sample-Product of Example No. | FTIR Frequency (cm$^{-1}$) |
|---|---|
| 18 | 1697.5 |
| 19 | N/A |
| 20 | 1699.2 |
| 21 | 1700.4 |
| 22 | 1699.4 |
| MS-Th (mono-succinimide-thermal PIBSA) | 1705.1 |
| BS-Th (bis-succinimide-chlorination PIBSA) | 1707.0 |
| MS-Cl (mono-succinimide-chlorination PIBSA) | 1706.2 |
| PS-Cl (polysuccinimide-chlorination PIBSA) | 1705.1 |
| CS-Cl (commercial succinimide-chlorination PIBSA) | 1705.1 |

N/A = not available.

TABLE VI

| | Sequence VE Engine Test Results - Sludge | |
|---|---|---|
| Sample 0.1 | Rocker Cover Sludge | Average Engine Sludge |
| Reference A | 1.2 | 3.8 |
| Reference A | 1.6 | 3.3 |
| Reference B | 8.6 | 8.9 |
| Reference B | 9.2 | 9.2 |
| Oil with 3% Product of Example 18 | 9.2 | 9.3 |
| Oil with 6% Product of Example 18 | 9.0 | 9.2 |

EXAMPLE 23

Preparation of Ethylene Carbonate Treated Bis TEPA Polysuccinimide with a High Degree of Polymerization To a 2 liter 3-necked flask equipped with an overhead stirrer, condensor and nitrogen inlet tube was added 677.0 g polyPIBSA, prepared according to Example 33, with a high degree of polymerization and 950 molecular weight polybutene tail (SAP No. 64.4, 0.389 mol). To this was added 267 g Chevron 100N diluent oil. This was then heated to 120° C. under nitrogen with stirring and 36.7 g TEPA (0.194 mol) was added rapidly. This was stirred for 4 hours at 160° C. A total of 5.8 cc. water was produced. This produced a bisTEPA polysuccinimide with a high degree of polymerization. Then the temperature was lowered to 80° C. and 102.43 g ethylene carbonate was added (1.16 mol). This amount was required so that two moles of ethylene carbonate reacted with each basic nitrogen in the bisTEPA polysuccinimide. The temperature was increased to 160° C. for 4 hours. A total of 1004.51 g of product was produced. The product had the following properties: Acid No.=0.08 mg KOH/g; % N=1.23%; Alkalinity Value=14.18 mg KOH/g; and viscosity at 100° C.=901.2 Cst.

EXAMPLE 24

Preparation of Ethylene Carbonate Treated Bis TEPA Polysuccinimide with a Low Degree of Polymerization To a 2 liter 3-necked flask equipped with an overhead stirrer, condensor and nitrogen inlet tube was added 497.0 g polyPIBSA prepared according to Example 17B with a low degree of polymerization and 950 molecular weight polybutene tail (Saponification No. 85.8, 0.38 mol). To this was added 447 g Chevron 100N diluent oil. This was then heated to 120° C. under nitrogen with stirring and 35.9 g TEPA (0.19 mol) was added rapidly. This was stirred for 4 hours at 160° C. A total of 5.9 cc. water was produced. This produced a bis-TEPA polysuccinimide with a low degree of polymerization. Then the temperature was lowered to 80° C. and 100.32 g ethylene carbonate was added (1.14 mol). This amount was required so that two moles of ethylene carbonate reacted with each basic nitrogen in the bis-TEPA polysuccinimide. The temperature was increased to 160° C. for 4 hours. A total of 1030.0 g of product was produced. The product had the following properties: Alkalinity Value 14.0 mg KOH/g.

EXAMPLE 25

Preparation of Borated Bis HPA Polysuccinimide with a High Degree of Polymerization To a 2 liter 3-necked flask equipped with an overhead stirrer, condensor and nitrogen inlet tube was added 864.0 g polyPIBSA made in a manner similar to Example 35, with a high degree of polymerization and 950 molecular weight polybutene tail (Saponification No. 49.0, 0.38 mol). To this was added 121 g Chevron 100N diluent oil. This was then heated to 140° C. under nitrogen with stirring and 52.3 g HPA (0.19 mol) was added rapidly. This was stirred for 4 hours at 170° C. A total of 7.5 cc. water was produced. This produced a bisHPA polysuccinimide with a high degree of polymerization. Then the temperature was lowered to 65° C. and 50 cc water and 27.09 g boric acid (0.44 mol) was added. This was heated at reflux (102° C.) for 2 hours, then the water was removed by distillation. The temperature was then increased to 171° C. for 2.5 hours. Then the product was decanted. The product had the following properties: Acid No.=2.30 mg KOH/g; % N=1.68%; % Boron=0.53; and viscosity at 100° C.=1014 Cst. It is anticipated that this borated product will have improved wear properties.

EXAMPLE 26

Preparation of Borated Bis TEPA Polysuccinimide with a Low Degree of Polymerization To a 2 liter 3-necked flask equipped with an overhead stirrer, condensor and nitrogen inlet tube was added 500 g polysuccinimide from Example 46. This was then heated to 50° C. under nitrogen with stirring and 50 ml water and 28.2 g boric acid (0.45 mol) was added. This was then heated at reflux (102° C.) for 2 hours. Then the water was distilled off, and the temperature was increased to 165° C. for 1.5 hours. A total of 517.0 g of product was produced. The product had the following properties: % N=1.24; viscosity at 100° C.=312.5 Cst; Acid No.=24.3 and % B=1.01%. It is anticipated that this borated product will have improved wear properties.

EXAMPLES 27 to 36

Table VII includes the results from additional preparations of polyPIBSA that were carried out using the basic synthetic procedure outlined in Examples 1 and 2. Table VII lists the reactants, reaction temperature, time and solvent and free radical initiator used as well as the weight of product and the saponification value.

TABLE VII

| Product of Example No. | Polybutene (g) | Maleic Anhydride (g) | Solvent (ml) | Initiator (g) | Temp. °C. | Time hrs | Weight Product (g) | Saponification value mg KOH/g Sample |
|---|---|---|---|---|---|---|---|---|
| 27 | Ultravis-10 (330) | 32.34 | chlorobenzene (210) | TBPB (1.2) | 138 | 30 | 345 | 51 |
| 28 | Ultravis-10 (330) | 32.34 | chlorobenzene (210) | TBPB (0.6) | 138 | 30 | 331 | 38 |
| 29 | Ultravis-30 (2171) | 164 | dichloroethane (1050) | TBPB (33) | 83 | 23 | 2265 | 55 |
| 30 | Ultravis-30 (4147) | 328 | chlorobenzene (1600) | DTBP (42.6) | 142 | 20 | 4429 | 67 |
| 31 | Ultravis-30 (4342) | 328 | dichloroethane (2000) | TBPB (66) | 83 | 22 | 4633 | 47 |
| 32 | Ultravis-10 (5000) | 515.8 | dichloroethane (3000) | DTBP (77.4) | 90 | 42 | 5506 | 46 |
| 33 | Ultravis-10 (5000) | 515.8 | dichloroethane (3000) | DTBP (77.4) | 91 | 92 | 5339 | 64.4 |
| 34 | Ultravis-30 (5000) | 376.9 | dichloroethane (3000) | DTBP (56.2) | 91 | 92 | 5350 | 34 |
| 35 | Ultravis-10 (2000) | 205.88 | dichloroethane (1200) | EDTBPB (96.8) | 91 | 29 | 2100 | 51 |
| 36 | Ultravis-30 (6000) | 453 | dichloroethane (3000) | TBPO (149.91) | 91 | 24 | 6272 | 50 |

TBPB = t-butylperoxybenzoate
DTBP = dit-butyl peroxide
TBPO = t-butyl peroctanoate
EDTBPB = ethyl-3,3-di(t-butyl peroxy)butyrate

EXAMPLES 37 to 48

Table VIII includes the results from additional preparations of polysuccinimides that were carried out using the basic synthetic procedure outlined in Examples 18-22. Table VIII lists the polyPIBSA used, the amount of diluent oil added, the polyamine used, the calculated charge mol ratio (CMR), the weight of final product, the water produced, and the % N.

TABLE VIII

| Example | PolyPIBSA Used (g) | Diluent Oil (g) | Polyamine Used (g) | CMR | Wt. of Product (g) | % N | ml H₂O Produced |
|---|---|---|---|---|---|---|---|
| 37 | Example 17B (500) | 443.9 | HPA (93.6) | 0.89 | 1025.7 | 2.94 | 6.2 |
| 38 | Example 17B (1000) | 1019 | TETA (55.8) | 0.5 | 2122.6 | 0.99 | 9.1 |
| 39 | Example 15 *(1280) | 696 | TETA (99.3) | 0.89 | 2060 | 1.79 | 15.0 |
| 40 | Example 31 **(1949) | 72 | TETA (55.8) | 0.5 | 1965.2 | 0.98 | 12 |
| 41 | Example 32 | 1881 | HPA | 0.5 | 3740 | 0.92 | 13 |

TABLE VIII-continued

| Example | PolyPIBSA Used (g) | Diluent Oil (g) | Polyamine Used (g) | CMR | Wt. of Product (g) | % N | ml H2O Produced |
|---|---|---|---|---|---|---|---|
| | (1776.8) | | (104.5) | | | | |
| 42 | Example 35 (1423.0) | 690 | TETA (110.96) | 0.89 | 2200 | 1.8 | 16.5 |
| 43 | Example 35 (1273) | 1697 | HPA (104.5) | 0.5 | 3060 | 1.13 | 14 |
| 44 | Example 31 (1403.6) | 500 | HPA (75.21) | 0.5 | 1965 | 2.14 | 13 |
| 45 | Example 36 (500) | 109 | HPA (28.88) | 0.5 | 606.3 | 1.50 | 3.6 |
| 46 | Example 17B (2500) | 2248 | TEPA (180.59) | 0.5 | 4879.2 | 1.4 | 31 |
| 47 | Example 35 (458) | 26.7 | TEPA (18.9) | 0.5 | 501.79 | 1.2 | 3.6 |
| 48 | Example 17B (261.62) | 209.11 | TEPA (32.89) | 0.87% | 497.34 | 2.2 | 2.6 |

*In this example, extra diluent oil (36%) was added to the polyPIBSA to make it easier to filter.
**In this example, extra diluent oil (18.4%) was added to the polyPIBSA to make it easier to filter.

EXAMPLE 49

Viton Seal Swell Test

Some lubricating oil additives have been identified as being deleterious to fluoroelastomers such as Viton that are currently used as gasket materials in automobile engines. European engine builders have now placed fluoroelastomer seal tests into their engine oil specifications. One such test is the Volkswagen VW3334 (September 1987) Seal Swell Test. This procedure is described in the Third Symposium of the European Coordination Council (CEC) 1989 in an article entitled "Engine and Bench Aging Effects on the Compatibility of Fluoroelastomers with Engine Oils" by Dr. S. W. Harris and J. C. Downey of Amoco Petroleum Additives Company.

The VW3334 (September 1987) Seal Swell Test was carried out on samples of Viton from the Parker Prudifa Company which were cut into dumbbell shapes, using a formulated lubricating test oil that contained succinimide dispersant, overbased detergent, antioxidant and viscosity index improver materials at a bath temperature of 150° C. for a 96 hour immersion time. The immersion procedure was similar to ASTM D471-79 Standard Test Method for Rubber Property-Effect of Liquids. Commercial succinimide dispersants were compared to the polysuccinimides of present Examples 47 and 48. The Viton samples were then subjected to analysis of their tensile properties using procedures similar to ASTM D412-87 Standard Test Method for Rubber Properties in Tension. The properties that were measured were cracking at 120 percent elongation, percent change in tensile strength and percent change in elongation at break, in accordance with the VW3334 Seal Swell Test requirements. The results are shown in Table IX.

The data in Table IX demonstrates that the polysuccinimide of Example 47 passed the Viton Seal Swell Test at the 0.07% nitrogen level, whereas the commercial bis-succinimide failed. Although the polysuccinimide of Example 48 did not pass the Viton test at the 0.13% nitrogen level, it performed better in this test than the commercial monosuccinimide at the 0.12% nitrogen level.

TABLE IX

| Sample | VITON SEAL SWELL TEST | | | |
|---|---|---|---|---|
| | Ts[1] | El[2] | Cr[3] | % N |
| Commercial monosuccinimide | −54 | −43 | Yes | 0.12 |
| Polysuccinimide, Example 48 | −49 | −39 | Yes | 0.13 |
| Commercial bis-succinimide | −29 | −23 | No | 0.07 |
| Polysuccinimide, Example 47 | −15 | −17 | No | 0.07 |
| passing limit | ±20 | ±25 | No | |

[1]Tensile strength % change
[2]Elongation to break % change
[3]Cracks, yes or no at 120% elongation

EXAMPLE 50

This example shows that after the copolymer of the present invention is formed, unreacted polybutene can be reacted with maleic anhydride to form thermal process PIBSA.

PolyPIBSA prepared in a manner similar to Example 17B having a Saponification No. of 86 was charged to a reactor and heated to 204° C. A molar equivalent of maleic anhydride (43.3 g), relative to unreacted non-vinylidene polybutene, was added and the mixture heated to 232° C. and held at this temperature for 4 hours. The temperature was reduced to 210° C. and the pressure was reduced to 28 inches of mercury. The reduced pressure and temperature was maintained for one hour. Then the mixture was filtered. The product had a Saponification No. of 88.

What is claimed is:

1. A copolymer of an unsaturated acidic reactant and a high molecular weight alkylvinylidene olefin having a sufficient number of carbon atoms such that the resulting copolymer is soluble in lubricating oil and wherein the olefin has at least about 1 branch per 2 carbon atoms along the chain.

2. A copolymer according to claim 1 wherein said unsaturated acidic reactant is of the formula:

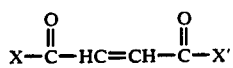

wherein X and X' are each independently selected from the group consisting of —OH, —Cl, —O—lower alkyl and when taken together, X and X' are —O—.

3. A copolymer according to claim 2 having an average degree of polymerization greater than 1.0.

4. A copolymer according to claim 3 wherein said olefin has an average molecular weight of about 500 to about 5000.

5. A copolymer according to claim 4 wherein said olefin is polyisobutene.

6. A copolymer according to claim 5 having an average degree of polymerization of about 1.5 to about 10.

7. A copolymer according to claim 6 wherein said acidic reactant comprises maleic anhydride.

8. A copolymer according to claim 7 wherein said polyisobutene has an average molecular weight of about 900 to about 2500.

9. A copolymer according to claim 8 wherein said alkylvinylidene isomer is methylvinylidene.

10. A fuel composition comprising a hydrocarbon boiling in a gasoline or diesel range and from about 30 to about 5000 parts per million of a copolymer according to claim 9.

11. A fuel concentrate comprising an inert stable oleophilic organic solvent boiling in the range of 150° F. to 400° F. and from about 5 to about 50 weight percent of a copolymer according to claim 9.

12. A lubricating oil composition comprising an oil of lubricating viscosity and a dispersant effective amount of a copolymer according to claim 9.

13. A lubricating oil concentrate comprising from about 90 to about 50 weight percent of an oil of lubricating viscosity and from about 10 to about 50 weight percent of a copolymer according to claim 9.

14. A copolymer of the formula:

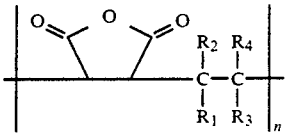

wherein n is 1 or greater, and $R_1$, $R_2$, $R_3$ and $R_4$ are selected from hydrogen, lower alkyl of 1 to 6 carbon atoms and high molecular weight polyalkyl; wherein either $R_1$ and $R_2$ are hydrogen and one of $R_3$ and $R_4$ is lower alkyl and the other is high molecular weight polyalkyl, or $R_3$ and $R_4$ are hydrogen and one of $R_1$ and $R_2$ is lower alkyl and the other is high molecular weight polyalkyl, and wherein the high molecular weight polyalkyl has at least about 1 branch per 2 carbon atoms along the chain.

15. A copolymer according to claim 14 wherein said high molecular weight polyalkyl comprises a polyisobutyl group of at least about 50 carbon atoms.

16. A copolymer according to claim 15 wherein said polyisobutyl group has an average molecular weight of about 500 to 5000.

17. A copolymer according to claim 16 wherein said polyisobutyl group has an average molecular weight of about 900 to 2500.

18. A copolymer according to claim 17 wherein having an average degree of polymerization of about 1.1 to about 20.

19. A copolymer according to claim 18 wherein said lower alkyl is methyl.

20. A product prepared by the process which comprises reacting a high molecular weight olefin wherein at least about 20 percent of the total high molecular weight olefin comprises an alkylvinylidene isomer and wherein said high molecular weight olefin has a sufficient number of carbon atoms such that said product is soluble in lubricating oil with an unsaturated acidic reactant in the presence of a free radical initiator, and wherein the high molecular weight olefin has at least about 1 branch per 2 carbon atoms along the chain.

21. A product prepared as in the process of claim 20 wherein said unsaturated acidic reactant is of the formula:

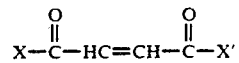

wherein X and X' are each independently selected from the group consisting of —OH, —Cl, —O—lower alkyl and when taken together, R and R' are —O—.

22. A product prepared as in the process of claim 21 wherein at least 50 percent of the total olefin comprises an alkylvinylidene isomer.

23. A product prepared as in the process of claim 20 wherein said high molecular weight olefin has an average molecular weight of about 500 to about 5000.

24. A product prepared as in the process of claim 23 wherein said high molecular weight olefin is polyisobutene.

25. A product prepared as in the process of claim 24 having an average degree of polymerization of about 1.5 to about 10.

26. A product prepared as in the process of claim 25 wherein said acidic reactant is maleic anhydride and said alkylvinylidene isomer is methylvinylidene.

27. A copolymer according to claim 1, 5 or 9 having a characteristic infrared succinic anhydride stretch in the range of about 1775 cm$^{-1}$ to about 1784 cm$^{-1}$ as measured by infrared spectroscopy.

28. A polysuccinimide prepared by reacting a copolymer according to claim 1, 5 or 9 with a polyamine having at least one basic nitrogen atom.

29. A polysuccinimide according to claim 28 having a characteristic infrared succinimide stretch in the range of about 1697 cm$^{-1}$ to about 1703 cm$^{-1}$ as measured by infrared spectroscopy.

30. A polysuccinimide according to claim 28 wherein said polyamine has from about 2 to about 12 amine nitrogen atoms and from about 2 to about 40 carbon atoms.

31. A polysuccinimide according to claim 30 wherein said polyamine has the formula $H_2N(YNH)_pH$ wherein Y is alkylene of 2 to 6 carbon atoms and p is an integer from 1 to 6.

32. A polysuccinimide according to claim 31 wherein the charge mole ratio of polyamine to succinic groups in copolymer is from about 1 to about 0.1.

33. A polysuccinimide according to claim 31 wherein the charge mole ratio of polyamine to succinic groups in copolymer is about 0.5.

34. A fuel composition comprising a hydrocarbon boiling in a gasoline or diesel range and from about 30 to about 5000 parts per million of an polysuccinimide according to claim 31.

35. A fuel concentrate comprising an inert stable oleophilic organic solvent boiling in the range of 150° F. to 400° F. and from about 5 to about 50 weight percent of a polysuccinimide according to claim 31.

36. A lubricating oil composition comprising an oil of lubricating viscosity and a dispersant effective amount of a polysuccinimide according to claim 31.

37. A lubricating oil concentrate comprising from about 90 to about 50 weight percent of an oil of lubricating viscosity and from about 10 to about 50 weight percent of a polysuccinimide according to claim 31.

38. A product prepared by the process which comprises reacting a polysuccinimide according to claim 28 having at least one primary or secondary amine group with a cyclic carbonate or a linear mono- or poly-carbonate.

39. The product according to claim 38, wherein the polysuccinimide is reacted with a cyclic carbonate.

40. The product according to claim 39, wherein the cyclic carbonate is ethylene carbonate.

41. A product prepared by the process which comprises reacting a polysuccinimide according to claim 28 with a boron compound selected from the group consisting of boron oxide, boron halide, boric acid and esters of boric acid.

42. The product according to claim 41, wherein the boron compound is boric acid.

43. A compound of the formula:

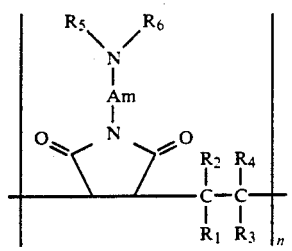

wherein n is one or greater, AM has from about 0 to about 10 amine nitrogen atoms and from about 2 to about 40 carbon atoms; and $R_1$, $R_2$, $R_3$ and $R_4$ are selected from hydrogen, lower alkyl of 1 to 6 carbon atoms and high molecular weight polyalkyl; wherein either $R_1$ and $R_2$ are hydrogen and one of $R_3$ and $R_4$ is lower alkyl and the other is high molecular weight polyalkyl, or $R_3$ and $R_4$ are hydrogen and one of $R_1$ and $R_2$ is lower alkyl and the other is high molecular weight polyalkyl; and $R_5$ and $R_6$ are independently hydrogen, lower alkyl of 1 to 6 carbon atoms, phenyl or taken together are alkylene of 3 to 6 carbon atoms to give a ring, and wherein the high molecular weight polyalkyl has at least about 1 branch per 2 carbon atoms along the chain.

44. A compound according to claim 43 wherein said high molecular weight polyalkyl comprises a polyisobutyl group of at least about 50 carbon atoms.

45. A compound according to claim 44 wherein said polyisobutyl group has an average molecular weight of about 500 to about 5000.

46. A compound according to claim 45 wherein Am has the formula wherein Z and Z' are independently alkylene of from 2 to 6 carbon atoms and p is an integer from 1 to 6, and $R_5$ and $R_6$ are hydrogen.

47. A compound according to claim 46 having an average degree of polymerization of about 1.1 to about 20.

48. A compound according to claim 47 wherein said polyisobutyl group has an average molecular weight of about 900 to about 2500.

49. A compound according to claim 48 wherein said lower alkyl is methyl.

50. A compound according to claim 49 having an average degree of polymerization of about 1.5 to about 10.

51. A compound according to claim 48 wherein Z and Z' are ethylene and p is 2, 3 or 4.

52. A fuel composition comprising a hydrocarbon boiling in a gasoline or diesel range and from about 30 to about 5000 parts per million of an compound according to claim 51.

53. A fuel concentrate comprising an inert stable oleophilic organic solvent boiling in the range of 150° F. to 400° F. and from about 5 to about 50 weight percent of a compound according to claim 51.

54. A lubricating oil composition comprising an oil of lubricating viscosity and a dispersant effective amount of a compound according to claim 51.

55. A lubricating oil concentrate comprising from about 90 to about 50 weight percent of an oil of lubricating viscosity and from about 10 to about 50 weight percent of a compound according to claim 51.

56. A random polysuccinimide comprising units selected from

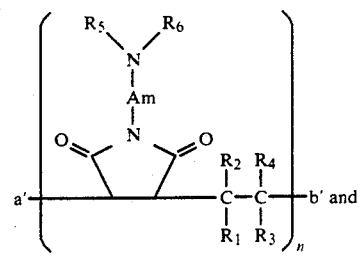

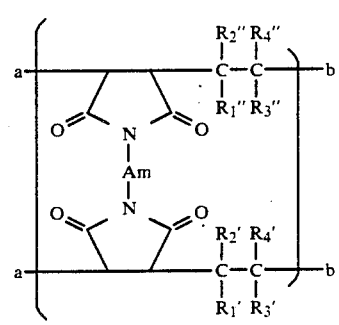

wherein Am is a linking group having from about 0 to 10 amine nitrogen atoms and from about 2 to 40 carbon atoms; $R_1$, $R_2$, $R_3$, $R_4$, $R_1'$, $R_2'$, $R_3'$, $R_4'$, $R_1''$, $R_2''$, $R_3''$, and $R_4''$ are selected from hydrogen, lower alkyl of one to 6 carbon atoms and high molecular weight polyalkyl; wherein either $R_1$ and $R_2$ are hydrogen and one of $R_3$ and $R_4$ is lower alkyl and the other is polyalkyl, or $R_3$ and $R_4$ are hydrogen and one of $R_1$ and $R_2$ is lower alkyl and the other is polyalkyl; either $R_1'$ and $R_2'$ are hydrogen and one of $R_3$ and $R_4$ is lower alkyl and the other is polyalkyl, or $R_3'$ and $R_4'$ are hydrogen and one of $R_1'$ and $R_2'$ is lower alkyl and the other is polyalkyl; and either $R_1''$ and $R_2''$ are hydrogen and one of $R_3''$ and $R_4'$ is lower alkyl and the other is polyalkyl or $R_3''$ and $R_4''$ are hydrogen and one of $R_1''$ and $R_2''$ is lower alkyl and the other is polyalkyl; $R_5$ and $R_6$ are independently hydrogen, lower alkyl of 1 to 6 carbon atoms, phenyl or taken together are alkylene of 3 to 6 carbon atoms to give a ring; and a, a', b and b' are sites for a covalent bond; provided that at least one a or a' site of each unit is covalently bonded to a b or b' site.

57. A random polysuccinimide according to claim 56 wherein said high molecular polyalkyl comprises a polyisobutyl group of at least about 50 carbon atoms.

58. A random polysuccinimide according to claim 57 wherein said polyisobutyl group has an average molecular weight of about 500 to 5000.

59. A random polysuccinimide according to claim 58 wherein Am has the formula $-[(ZNH)_pZ']-$ wherein Z is alkylene of 2 to 6 carbon atoms, Z' is alkylene of 2 to 6 carbon atoms and p is an integer from 0 to 5, and $R_5$ and $R_6$ are hydrogen.

60. A random polysuccinimide according to claim 59 wherein the average sum of A and B units is from about 2 to about 50.

61. A random polysuccinimide according to claim 60 wherein said polyisobutyl group has an average molecular weight of about 900 to about 2500.

62. A random polysuccinimide according to claim 61 wherein said lower alkyl is methyl.

63. A random polysuccinimide according to claim 62 comprising from about 2 to about 10 times as many B units as A units.

64. A random polysuccinimide according to claim 63 wherein Z and Z' are ethylene and p is 1, 2 or 3.

65. A fuel composition comprising a hydrocarbon boiling in a gasoline or diesel range and from about 30 to about 5000 parts per million of an random polysuccinimide according to claim 64.

66. A fuel concentrate comprising an inert stable oleophilic organic solvent boiling in the range of 150° F. to 400° F. and from about 5 to about 50 weight percent of a random polysuccinimide according to claim 64.

67. A lubricating oil composition comprising an oil of lubricating viscosity and a dispersant effective amount of a random polysuccinimide according to claim 64.

68. A lubricating oil concentrate comprising from about 90 to about 50 weight percent of an oil of lubricating viscosity and from about 10 to about 50 weight percent of a random polysuccinimide according to claim 64.

* * * * *